(12) United States Patent
Summers et al.

(10) Patent No.: US 8,023,710 B2
(45) Date of Patent: Sep. 20, 2011

(54) VIRTUAL COLONOSCOPY VIA WAVELETS

(75) Inventors: Ronald M. Summers, Potomac, MD (US); Jiang Li, Virginia Beach, VA (US); Sharon Greenblum, Kensington, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1223 days.

(21) Appl. No.: 11/685,127

(22) Filed: Mar. 12, 2007

(65) Prior Publication Data
US 2008/0194946 A1    Aug. 14, 2008

Related U.S. Application Data

(60) Provisional application No. 60/889,489, filed on Feb. 12, 2007.

(51) Int. Cl.
G06K 9/00 (2006.01)
G06K 9/62 (2006.01)
A61B 5/05 (2006.01)

(52) U.S. Cl. ........ 382/131; 382/130; 382/128; 382/132; 382/133; 382/159; 382/181; 382/224; 600/425

(58) Field of Classification Search .................. 382/131, 382/130, 128, 132, 133, 159, 181, 224; 600/425
See application file for complete search history.

(56) References Cited

U.S. PATENT DOCUMENTS

| | | | |
|---|---|---|---|
| 5,598,481 A | 1/1997 | Nishikawa et al. | |
| 5,666,434 A | 9/1997 | Nishikawa et al. | |
| 5,673,332 A | 9/1997 | Nishikawa et al. | |
| 5,740,268 A | 4/1998 | Nishikawa et al. | |
| 5,971,767 A | 10/1999 | Kaufman et al. | |
| 6,078,680 A | 6/2000 | Yoshida et al. | |
| 6,081,612 A * | 6/2000 | Gutkowicz-Krusin et al. | 382/128 |

(Continued)

FOREIGN PATENT DOCUMENTS
WO    WO 03058553 A2 *  7/2003

OTHER PUBLICATIONS

Karkanis, et al. "Computer-Aided Tumor Detection in Endoscopic Video Using Color Wavelet Features." IEEE Transactions on Information Technology in Biomedicine. 7.2 (2003): 141-152.*

(Continued)

Primary Examiner — Matthew C Bella
Assistant Examiner — Michael A Newman
(74) Attorney, Agent, or Firm — Klarquist Sparkman, LLP

(57) ABSTRACT

Various techniques can be used to improve classification of colon polyps candidates found via computed tomographic colonography computer aided detection (CTCCAD). A polyp candidate can be classified as a true positive or a false positive. For example, a two-dimensional projection image of the polyp can be generated from a three-dimensional representation and classified based on features of the projection image. An optimal viewpoint for the projection image can be found via techniques such as maximizing viewpoint entropy. Wavelet processing can be used to extract features from the two-dimensional projection image. Feature extraction can use a piecewise linear orthonormal floating search for locating most predictive neighbors for wavelet coefficients, and support vector machines can be employed for classification. The techniques can be useful for improving accuracy of CTCCAD techniques.

13 Claims, 36 Drawing Sheets

U.S. PATENT DOCUMENTS

| | | | |
|---|---|---|---|
| 6,246,784 B1 | 6/2001 | Summers et al. | |
| 6,331,116 B1 | 12/2001 | Kaufman et al. | |
| 6,343,936 B1 | 2/2002 | Kaufman et al. | |
| 6,345,112 B1 | 2/2002 | Summers et al. | |
| 6,556,696 B1 | 4/2003 | Summers et al. | |
| 7,057,615 B2 | 6/2006 | Wang et al. | |
| 7,260,250 B2 | 8/2007 | Summers et al. | |
| 7,397,936 B2 * | 7/2008 | Periaswamy | 382/128 |
| 7,440,601 B1 | 10/2008 | Summers et al. | |
| 7,454,045 B2 | 11/2008 | Yao et al. | |
| 7,558,413 B2 * | 7/2009 | Tu et al. | 382/128 |
| 7,646,904 B2 | 1/2010 | Summers et al. | |
| 2001/0031920 A1 * | 10/2001 | Kaufman et al. | 600/431 |
| 2003/0007683 A1 | 1/2003 | Wang et al. | |
| 2003/0025713 A1 | 2/2003 | Wang et al. | |
| 2003/0223627 A1 | 12/2003 | Yoshida et al. | |
| 2004/0064029 A1 | 4/2004 | Summers et al. | |
| 2005/0078858 A1 * | 4/2005 | Yao et al. | 382/128 |
| 2005/0105801 A1 * | 5/2005 | Periaswamy | 382/192 |
| 2005/0107695 A1 * | 5/2005 | Kiraly et al. | 600/431 |
| 2005/0117787 A1 | 6/2005 | Iordanescu et al. | |
| 2005/0119550 A1 * | 6/2005 | Serra et al. | 600/407 |
| 2005/0152588 A1 | 7/2005 | Yoshida et al. | |
| 2005/0152591 A1 * | 7/2005 | Kiraly et al. | 382/131 |
| 2006/0290698 A1 | 12/2006 | Wang et al. | |
| 2007/0127803 A1 | 6/2007 | Yoshida et al. | |
| 2007/0127804 A1 | 6/2007 | Yoshida et al. | |
| 2007/0165928 A1 | 7/2007 | Yoshida et al. | |
| 2008/0008367 A1 | 1/2008 | Franaszek et al. | |
| 2008/0015419 A1 | 1/2008 | Summers et al. | |
| 2008/0055308 A1 * | 3/2008 | Dekel et al. | 345/421 |
| 2008/0304616 A1 | 12/2008 | Van Uitert, Jr. et al. | |
| 2009/0208409 A1 | 8/2009 | Summers et al. | |
| 2010/0074491 A1 | 3/2010 | Summers et al. | |

OTHER PUBLICATIONS

Dehmeshki et al. "Multiresolution Active Contour Model Applied on Lung and Colon Images." Medical Imaging 2004:Proceedings of the SPIE. 5370. (2004): 1685-1694.*

Jerebko, et al. "Computer-aided polyp detection in CT colonography using an exemble of support vector machines." International Congress Series. 1256. (2003): 1019-1024.*

Vazquez, et al. "Viewpoint Selection Using Viewpoint Entropy." Proceedings of Vision Modeling and Visualization Conference. (2001): 273-280.*

Lyu, et al. "A Digital Technique for Art Authentication." PNAS. 101.49 (2004): 17006-17010.*

Li et al. "Wavelet Method for CT Colonography Computer-Aided Polyp Detection." Proceedings of ISBI 2006. (2006): 1316-1319.*

Gokturk, et al. "A New 3-D Volume Processing Method for Polyp Detection." Engineering in Medicine and Biology Society, 2001. Proceedings of the 23rd Annual International Conference of the IEEE . 3. (2001): 522-2525.*

Karkanis et al. "Computer-Aided Tumor Detection in Endoscopic Video Using Color Wavelet Features." IEEE Transactions on Information Technology in Biomedicine. 7.2 (2003): 141-152.*

Lyu et al. "A Digital Technique for Art Authentication." PNAS. 101.49 (2004): 17006-17010.*

Vazquez et al. "Viewpoint Selection Using Viewpoint Entropy." Proceedings of Vision Modeling and Visualization Conference (2001): 273-280.*

Jerebko et al. "Computer-aided polyp detection in CT colonography using an ensemble of support vector machines." International Congress Series. 1256. (2003): 1019-1024.*

Vazquez, et al. "Fast Adaptive Selection of Best Views." ICCSA 2003, LNCS. 2669. (2003): 295-305.*

Ji, et al. "Dynamic View Selection for Time-Varying Volumes." IEEE Transactions on Visualization and Computer Graphics. 12.5 (2006): 1109-1116.*

Carrion, et al. "Could the Pollen Origin be Determined using Computer Vision? An Experimental Study." Visualization, Imaging, and Image Processing. (2002): 1-6.*

U.S. Appl. No. 10/961,681, filed Oct. 10, 2003, Summers et al.

Dehmeshki et al., "Multiresolution Active Contour Model Applied on Lung and Colon Images," In *Medical Imaging 2004:Proceedings of SPIE* vol. 5370 pp. 1685-1694, 2004, 10 pages.

Dehmeshki et al., "Multiresolution Active Contour Model: Application to Lung and Colon Images," *Biomedical Engineering; Proceedings of the Second International Conference*, Feb. 16-18, 2004, pp. 332-336, 5 pages.

Eddy, "Screening for Colorectal Cancer," *Ann. Intern. Med.*, vol. 113, pp. 373-384, 1990, 12 pages.

Greenblum et al., "Wavelet Analysis in Virtual Colonoscopy," in (*SPIE*) *Medical Imaging 2006: Physiology, Function, and Structure from Medical Images*, vol. 6143, pp. 992-999, Mar. 13, 2006, 8 pages.

Greenblum et al., "Wavelet Analysis in Virtual Colonscopy," abstract, handed to attendees of SPIE Medical Imaging Conference on or after Feb. 11, 2006, 1 page.

Greenblum et al., "Wavelet Analysis in Virtual Colonscopy," poster, displayed in hall during SPIE Medical Imaging Conference, about 500 attendees, on or after Feb. 12, 2006, 1 page.

Gumhold, "Maximum Entropy Light Source Placement," *IEEE Visualization*, 2002, pp. 275-282, 8 pages.

Hubbard, *The World According to Wavelets*, 2nd Ed., Chapter IV: Applications, 1998, 37 pages.

Iakovidis et al., "Texture Multichannel Measurements for Cancer Precursors' Identification Using Support Vector Machines," *Measurement* 36 (2004) 297-313, Oct. 2004, 17 pages.

Iordanescu and R.M. Summers, "Automated Centerline for Computed Tomography Colonography," *Academic Radiol.*, vol. 10, pp. 1291-1301, 2003, 11 pages.

Jafari-Khouzani et al., "Texture Analysis of hippocampus for epilepsy," *In Medical Imaging 2003: Proceedings of SPIE* vol. 5031 pp. 279-288, 2003, 10 pages.

Karkanis et al., "Computer-Aided Tumor Detection in Endoscopic Video Using Color Wavelet Features," *IEEE Transactions on Information Technology in Biomedicine*, vol. 7, No. 3, Sep. 2003, 12 pages.

Li et al., "An Efficient Feature Selection Algorithm for Computer-Aided Polyp Detection," Florida Artificial Intelligence Research Society (FLAIRS) Conference, May 2005, also in *International Journal on Artificial Intelligence Tools* 15(6): 893-916, Dec. 2006, 6 pages.

Li et al., "Feature Selection Using a Piecewise Linear Network," IEEE Transactions on Neural Networks, vol. 17, No. 5, Sep. 2006, 15 pages.

Li et al., "Wavelet Method for CT Colonography Computer-Aided Polyp Detection," In *Proceedings of ISBI 2006*, Apr. 2006, pp. 1316-1319, 4 pages.

Lyu et al., "A Digital Technique for Art Authentication," PNAS, vol. 101, No. 49, Dec. 7, 2004, 5 pages.

Metz et al., ROCKIT software description, http://www-radiology.uchicago.edu/krl.KRL_ROC/software_index6.htm, Kurt Rossmann Laboratories, University of Chicago, visited Mar. 6, 2007, 5 pages.

Miller et al., "Feature Selection for Computer-Aided Polyp Detection using Genetic Algorithms," *In Medical Imaging 2003 Proceedings of SPIE* vol. 5031, 2003, pp. 102-110, 9 pages.

Pickhardt et al., "Computed Tomographic Virtual Colonoscopy to Screen for Colorectal Neoplasia in Asymptomatic Adults," *New Engl. J.Med.*, 349:2191 (2003), 10 pages.

Platt, "Probabilistic Outputs for Support Vector Machines and Comparisons to Regularized Likelihood Methods," *Advances in Large Margin Classifiers*, MIT Press, 1999, 11 pages.

Pun and Lee, "Log-Polar Wavelet Energy Signatures for Rotation and Scale Invariant Texture Classification," *IEEE. Tran. Pat. Ana. Mach. Intel.*, vol. 25, 2003, pp. 590-603, 14 pages.

Summers et al., Automated Polyp Detector for CT Colonography: Feasibility Study *Radiology*; 216: (2000) pp. 284-290, 7 pages.

Takahashi et al., "A Feature-Driven Approach to Locating Optimal Viewpoints for Volume Visualization," *Proceedings of IEEE Visualization 2005*, 2005, pp. 495-502, 8 pages.

Van Uitert et al., "Subvoxel Precise Skeletons of Volumetric Data Based on Fast Marching Methods," Med Phys. 34(2), pp. 627-638, Feb. 2007, 12 pages.

Vazquez et al., "Viewpoint Selection Using Viewpoint Entropy," in *Proceedings of Vision Modeling and Visualization Conference* (VMV 2001), 2001, pp. 273-280, 8 pages.

Vining et al., "Virtual Bronchoscopy. Relationships of Virtual Reality Endobronchial Simulations to Actual Bronchoscopic Findings" *Chest* 109(2): 549-553 (Feb. 1996) 7 pages.

Vining et al., "Virtual Colonoscopy," Radiology 193(P):446(1994) 1 page.

Vining et al., "Virtual Bronchoscopy," Radiology 193(P):261 (1994) 1 page.

"Wavelet," Wikipedia, www.wikipedia.org, last modified Feb. 3, 2007, 9 pages.

Li et al., "Wavelet method for CT colonography computer-aided polyp detection," *Med. Phys.*, vol. 35, Issue 8, (Aug. 2008) pp. 3527-3538.

Sun et al., "Assessment of VIE image quality using helical CT angiography: in vitro phantom study," *Computerized Medical Imaging and Graphics*, vol. 28, Issue 1, (Jan. 2004), pp. 3-12.

\* cited by examiner

General Scaling function
$$\phi(t) = 2\sum h_0(k)\phi(2t-k)$$
General Wavelet equation
$$\psi(t) = 2\sum h_1(k)\phi(2t-k)$$

Haar scaling function
$$\phi(t) = \phi(2t) + \phi(2t-1)$$
Haar wavelet equation
$$\psi(t) = \phi(2t) - \phi(2t-1)$$

B (a) 0.6cm, Score = 0.18  (b) 0.8cm, Score = 0.495  (c) 0.6cm, Score = 0.40

(a)

(b)

(c)

(d)

VIRTUAL COLONOSCOPY VIA WAVELETS

CROSS-REFERENCE TO RELATED APPLICATIONS

This application claims the benefit of U.S. Provisional Patent Application No. 60/889,489 filed on Feb. 12, 2007, entitled "WAVELET ANALYSIS IN VIRTUAL COLONOSCOPY," which is hereby incorporated herein by reference.

TECHNICAL FIELD

The field relates to software analysis of images in a medical context.

BACKGROUND

Although colon cancer is the second leading cause of cancer death in the United States, it is also often treatable. Early detection of colon polyps is a key to treatment. CT colonography (CTC), also known as virtual colonoscopy, is a promising new non-intrusive detection technique where polyps are identified from CT scans, sometimes with the aid of a computer-aided detection (CAD) system.

However, virtual colonoscopy can be plagued by false positives. False positives are troublesome because any identified positives must be considered and evaluated by a human classifier such as a physician or technologist. Even if a feature can be quickly dismissed as a false positive, too many false positives consume an inordinate amount of time and limit the usefulness of the software-based approach.

Thus, more work is needed to increase specificity by filtering out false positives and otherwise improving virtual colonoscopy technologies.

SUMMARY

Digital representations of portions of an anatomical structure associated with polyp candidates can be processed to determine whether they are indeed polyps. For example, polyp candidates identified by software can be filtered by a post-processing technique.

After a polyp candidate is identified in a three-dimensional representation of the colon, a two-dimensional projection image of the polyp candidate can be processed by various technologies to determine whether the polyp candidate is a polyp.

As described herein, wavelet-based technologies can be applied in the determination. For example, wavelet-based features can be evaluated.

Generation of a two-dimensional projection image can be accomplished by choosing a viewpoint via viewpoint entropy techniques. For example, a point along the centerline of a colon can be selected as a viewpoint for a virtual camera which takes a snapshot of the polyp candidate. Virtual lighting can be applied.

When choosing a viewpoint, background information for the polyp candidate can be ignored. Viewpoint entropy can be computed directly from faces of a mesh for the polyp candidate.

Most predictive neighbor techniques can be applied to improve feature extraction. For example, a piecewise linear orthonormal floating search can find most predictive neighbors.

Classification via the extracted features can be accomplished via support vector machines (SVM's). For example, a committee of SVM's can be employed to evaluate the features. SVM training can proceed by determining which features best impact scores provided by the SVM. Different members of the committee can consider different wavelet features.

Additional features and advantages of the technologies described herein will be made apparent from the following detailed description of illustrated embodiments, which proceeds with reference to the accompanying drawings.

BRIEF DESCRIPTION OF THE DRAWINGS

FIG. 25 is a mathematical description of wavelets.

DETAILED DESCRIPTION

Overview of Technologies

The technologies described herein can be used in any of a variety of scenarios in which determining whether a polyp candidate is a polyp is useful. For example, when performing computer-aided detection of polyps in a CT scan of the colon, determining whether a polyp candidate is a polyp can help reduce the number of false positives.

A digital representation includes any digital representation of an anatomical structure (or portion thereof) stored for processing in a digital computer. For example, representations can include two- or three-dimensional representations (e.g., one or more images) of portions of an anatomical structure stored via a variety of data structures. Representations can be composed of pixels, voxels, or other elements. A digital representation of an anatomical structure is sometimes called "virtual" (e.g., a "virtual colon") because it is a digital representation that can be analyzed to learn about the represented anatomical structure.

A component of a digital representation includes any two- or three-dimensional element that composes a part of a representation of a portion of an anatomical structure stored as an image. For example, pixels and voxels can be components.

Segmenting includes the process of dividing a digital representation of an anatomical structure into constituent parts into which a body, entity, or quantity is divided or marked off by or as if by natural boundaries. Common types of segmentation include freehand segmentation, region-based (or region-growing) segmentation, fuzzy connectedness segmentation, K-means clustering segmentation, level set segmentation, active contours segmentation, expectation-maximization segmentation, and so on.

Imaging includes any technologies for obtaining an image of the inside of a body by transmitting electromagnetic or sonic waves through the body. Imaging includes radiographic images (with X-rays, for example computer tomography or "CT"), sonic energy (such as ultrasound) and magnetic fields (such as magnetic resonance imaging, or "MRI"). Although representations of an anatomical structure using such technology are sometimes called an "image," in practice, the representation can be a series of image slices.

Exemplary anatomical structures in any of the examples herein include such structures as the colon, heart, bronchi, blood vessels, biliary tract, urinary tract, and esophagus.

Example 1

Exemplary System Configured to Determine Whether a Polyp Candidate is a Polyp

Figure 1:
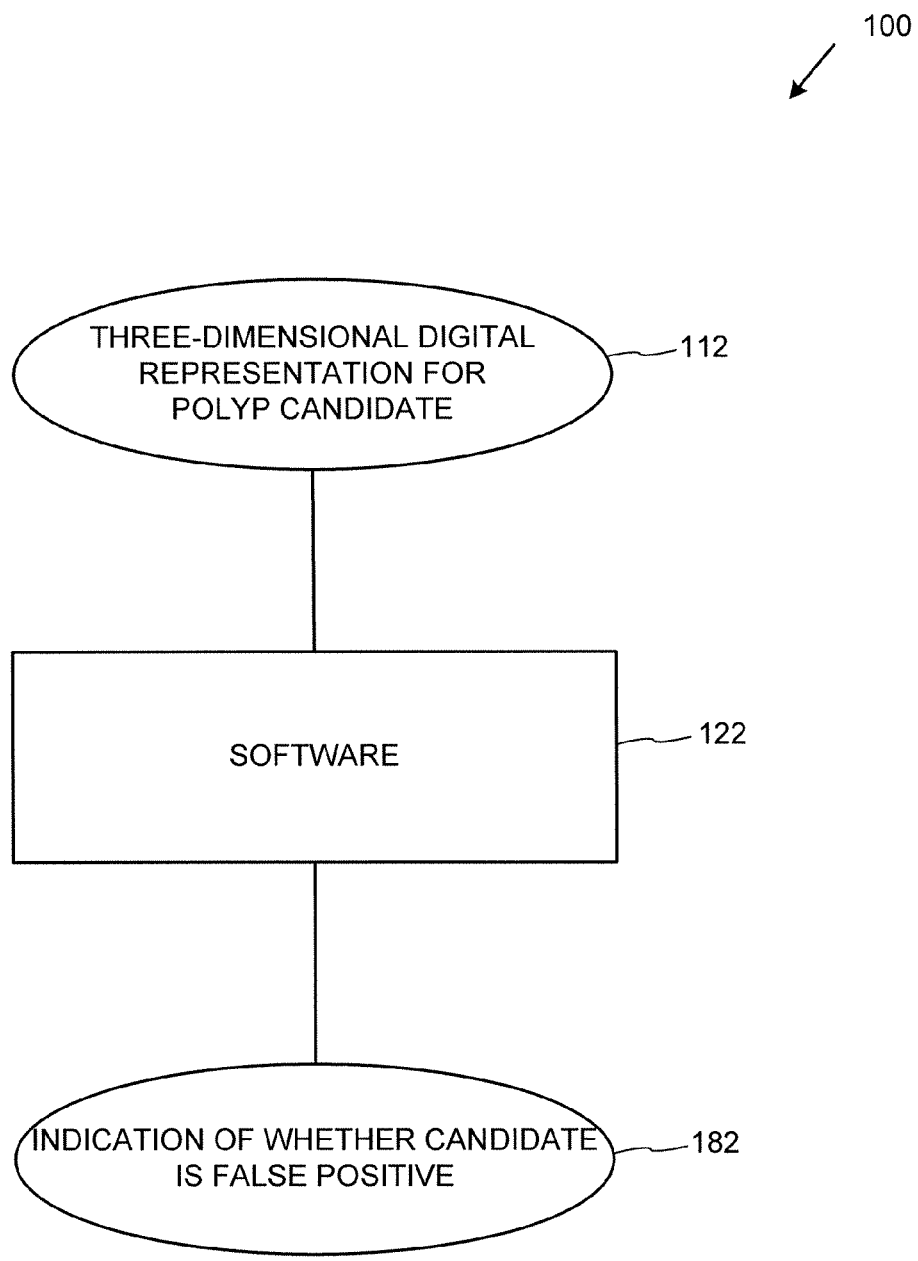
FIG. 1 is a block diagram of an exemplary system configured to process a three-dimensional representation for a polyp candidate and determine whether the polyp candidate is a false positive.

FIG. 1 shows an exemplary system 100 configured to determine whether a polyp candidate is a polyp. In the example, a three-dimensional digital representation for a polyp candidate 112 is processed by software 122, which outputs an indication 182 of whether the polyp candidate is a polyp.

Example 2

Exemplary Method of Determining Whether a Polyp Candidate is a Polyp

Figure 2:
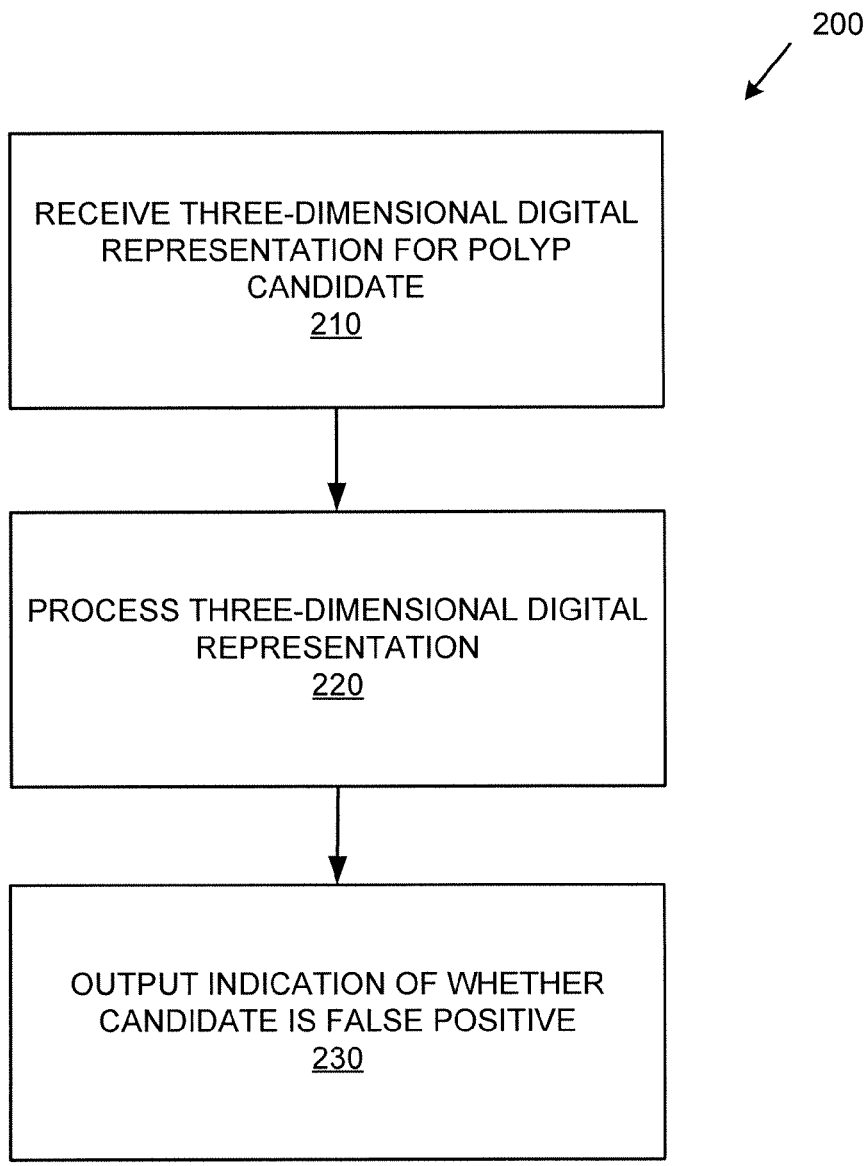
FIG. 2 is a flowchart of an exemplary method of processing a three-dimensional representation for a polyp candidate to output an indication of whether a polyp candidate is a false positive.

FIG. 2 is a flowchart of an exemplary method 200 of processing a three-dimensional representation of a polyp candidate to output an indication of whether a polyp candidate is a false positive. The method 200 can be implemented, for example, in a system such as that shown in FIG. 1.

At 210, a three-dimensional digital representation for a polyp candidate is received. At 220, the three-dimensional digital representation is processed. For example, any of the classification technologies described herein can be applied to the representation of the polyp candidate.

At 230, an indication of whether the polyp candidate is a polyp is outputted.

Example 3

Exemplary Polyp Candidates

As described herein, a polyp candidate can be any portion of an anatomical structure that has been determined to possibly contain a polyp (e.g., by software that evaluates a virtual anatomical structure for polyps). In practice, the polyp candidate can be specified by a location within the anatomical structure (e.g., via coordinates or some other mechanism). Software can provide a list of one or more polyp candidates that can be processed by the technologies described herein to determine whether they are indeed polyps or false positives. Polyp candidates are sometimes called "polyp detections" herein.

Example 4

Exemplary Three-Dimensional Representation for Polyp Candidate

In any of the examples herein, a three-dimensional representation for a polyp candidate can include a portion of a three-dimensional representation of an anatomical structure. In practice, the representation for the polyp candidate can include more than the polyp itself (e.g., portions of the anatomical structure surrounding the polyp). However, analysis can proceed by determining the portions of the three-dimensional representation that correspond to the polyp (or polyp candidate).

The three-dimensional representation can be received as an indication of where within a three-dimensional representation of an anatomical structure the polyp candidate resides. For example, a location (e.g., estimated center of the polyp candidate or the like) within the three-dimensional representation of the anatomical structure can be received.

In practice, a list of polyp candidates can be provided. The techniques described herein can be applied to filter the list of polyp candidates to those classified as polyps (e.g., true positive, not a false positive, or the like).

Additional information (e.g., an initial confidence score, estimated size, initial classification, or the like) can be included with the three-dimensional representation of the polyp candidate if desired.

Any of the imaging technologies described herein can be used to generate the three-dimensional digital representations described herein.

Example 5

Exemplary Determination of Whether a Polyp Candidate is a Polyp

In any of the examples herein, software can determine whether a polyp candidate is a polyp. Such a scenario can alternatively be described as determining whether a polyp candidate is a false positive, determining whether the polyp candidate is a true positive, determining whether the polyp candidate is a true polyp, determining whether the polyp candidate is a true negative, classifying the polyp candidate, and the like.

Example 6

Exemplary Indication of Whether a Polyp Candidate is a Polyp

In any of the examples herein, an indication of whether a polyp candidate is a polyp (e.g., classified as a polyp by the software) can be provided. Any of the technologies described herein can be applied to increase accuracy of the indication. Even a small increase in accuracy can be significant because some detection techniques can result in a large number of candidates. Thus, an indication of whether the polyp candidate is a polyp can be used to filter out false positives and reduce the burden on a human classifier who reviews a list of polyps provided by the technologies. To the human classifier, the polyp candidates classified as polyps can be considered polyp candidates for which a final determination is made.

In any of the examples, an indication of whether a polyp candidate is a polyp can be an internal indication (e.g., outputted from one part of software to another), an external indication (e.g., an indication displayed on a computer user interface), or an implied indication (e.g., a polyp candidate determined to be a false positive is removed from a list of candidates, a polyp candidate determined to be a true positive is added to a list of confirmed candidates, or the like).

The indication can be expressed alternatively as whether the polyp candidate is a false positive, whether the polyp candidate is a true positive, or the like.

Example 7

Figure 3:
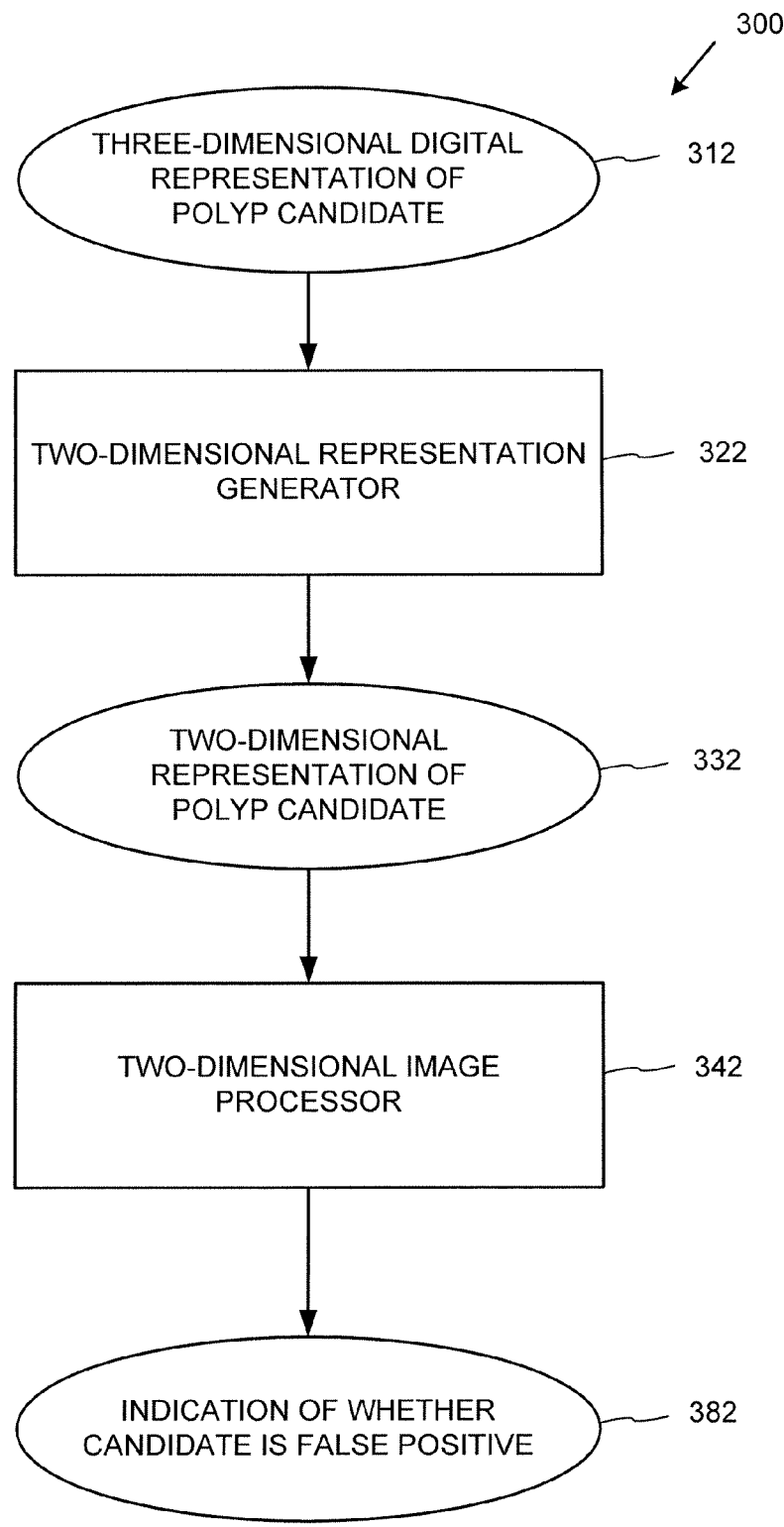
FIG. 3 is a block diagram of an exemplary system configured to generate a two-dimensional representation of a polyp candidate and determine whether the polyp candidate is a polyp.

Exemplary System Configured to Generate a Two-dimensional Representation of a Polyp Candidate and Determine Whether the Polyp Candidate is a Polyp FIG. 3 shows an exemplary system 300 configured to generate a two-dimensional representation 332 of a polyp candidate and determine whether the polyp is a polyp candidate is a polyp.

The system receives a three-dimensional digital representation 312 of a polyp candidate as input. A two-dimensional representation generator 322 is configured to generate a two-dimensional representation 332 of the polyp candidate depicted in the three-dimensional representation 312.

A two-dimensional image processor 342 is configured to output an indication 382 of whether the polyp candidate is a polyp.

Example 8

Figure 4:
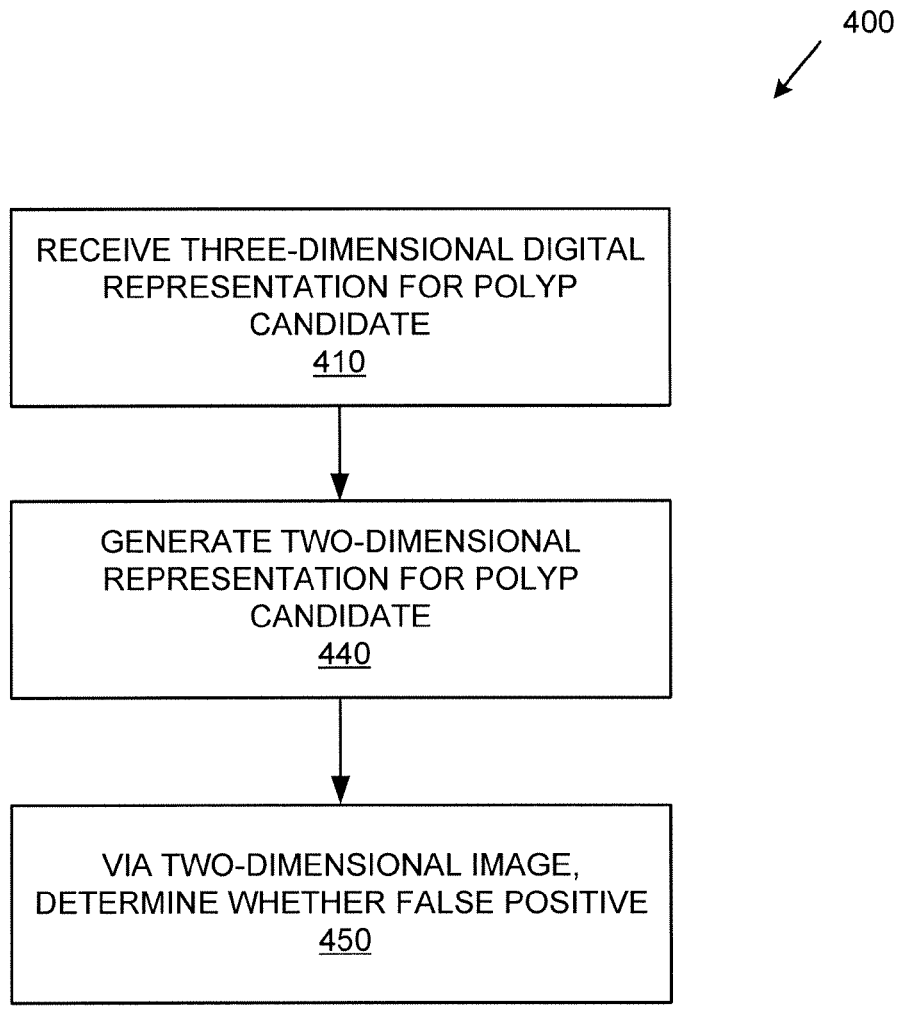
FIG. 4 is a flowchart of an exemplary method of generating a two-dimensional representation of a polyp candidate and determining whether the polyp candidate is a polyp.

Exemplary Method of Generating Two-dimensional Representation and Determining Whether Candidate is a Polyp FIG. 4 shows an exemplary method 400 of generating a two-dimensional representation of a polyp candidate and determining whether the polyp candidate is a polyp. The method 400 can be implemented, for example, by a system such as that shown in FIG. 3.

At 410 a three-dimensional digital representation for a polyp candidate is received. At 440, a two-dimensional representation for the polyp candidate is generated.

At 450, via the two-dimensional image, a determination is made regarding whether the polyp candidate is a polyp. As described herein, making the determination can comprise applying wavelet-based technologies.

Subsequently, an indication of the determination can be provided as output as described herein. Additional actions can be taken responsive to the determination.

Example 9

Exemplary Two-dimensional Representation of Polyp Candidate

In any of the examples herein describing a two-dimensional representation of a polyp candidate, the two-dimensional representation of the polyp candidate can be a projection image or the like generated from a three-dimensional representation of the polyp candidate. As described herein, the two-dimensional representation can be generated via any of the projection technologies described herein or the like. In some cases the projection image is called a "snapshot" because it can be generated via a virtual camera pointed at the three dimensional representation of the polyp candidate.

In practice, the image can be an endoluminal projection image. The image can include background information, such as portions of an anatomical structure surrounding the polyp, folds, or the like.

Example 10

Figure 5:
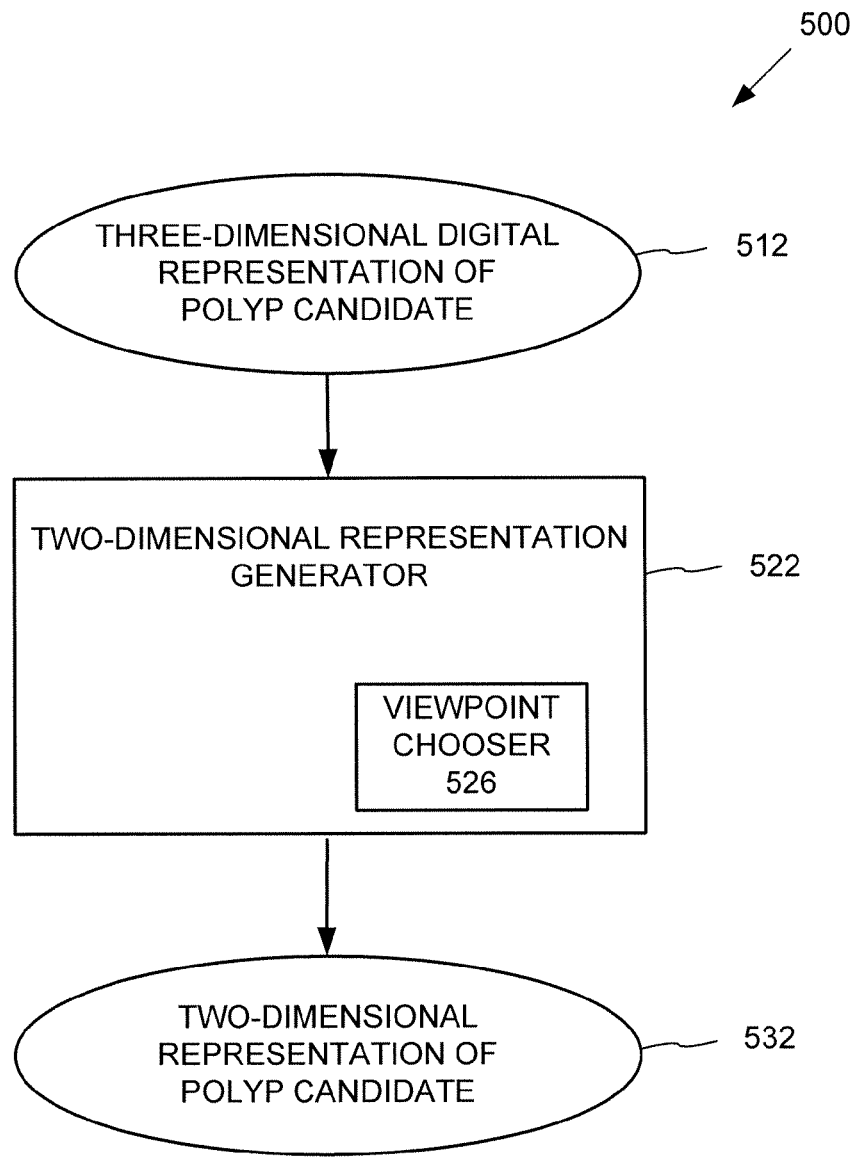
FIG. 5 is a block diagram of an exemplary system configured to generate a two-dimensional representation of a polyp candidate via a viewpoint chooser.

Exemplary System Configured to Generate Two-Dimensional Representation Via Viewpoint Chooser FIG. 5 is a block diagram of an exemplary system 500 configured to generate a two-dimensional representation 532 of a polyp candidate via a viewpoint chooser 526. The system 500 takes a three-dimensional digital representation 512 of a polyp candidate as input. A two-dimensional representation generator 522 can output a two-dimensional representation 532 of the polyp candidate by employing a viewpoint chooser 526.

The viewpoint chooser 526 can be configured to use an optimal viewpoint selection technique to select a viewpoint for the three-dimensional digital representation 512 and generate the two-dimensional representation 532 with the viewpoint via any of the two-dimensional image generation techniques described herein.

Example 11

Exemplary Method of Choosing Viewpoint

Figure 6:
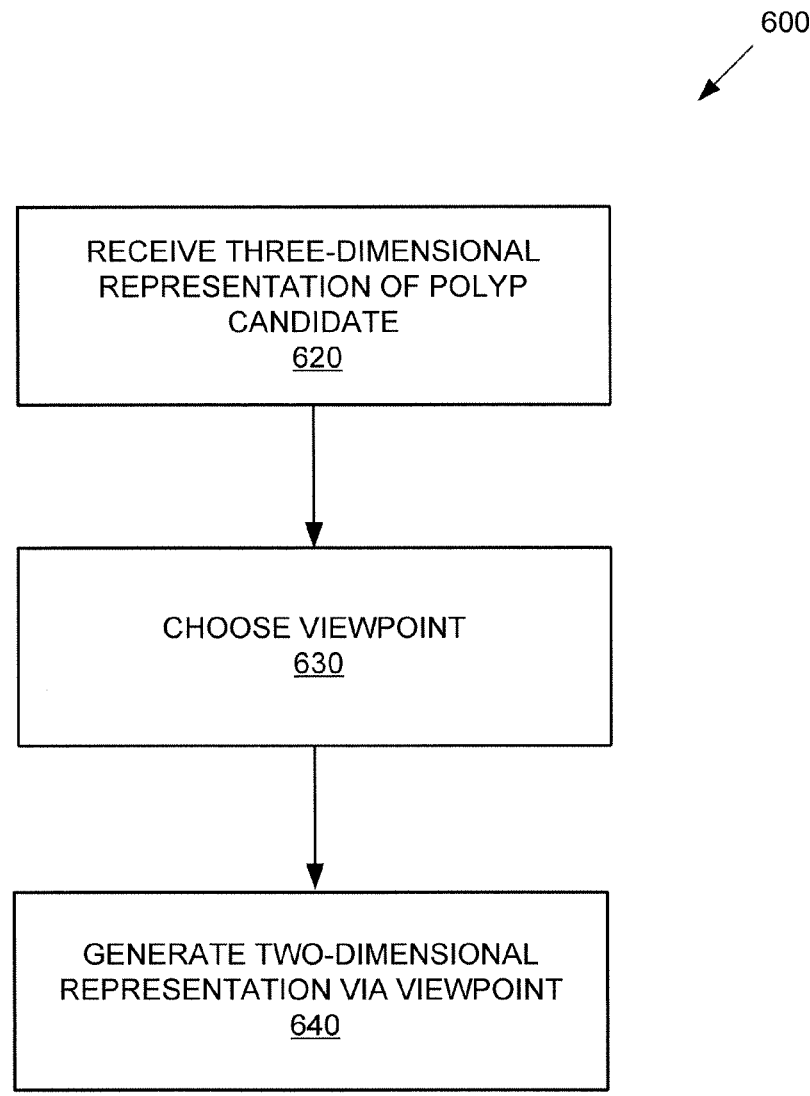
FIG. 6 is a flowchart of an exemplary method of choosing a viewpoint for generating a two-dimensional representation of a polyp candidate.

FIG. 6 is a flowchart of an exemplary method 600 of choosing a viewpoint for generating a two-dimensional representation of a polyp candidate. The method 600 can be implemented, for example in a system such as that shown in FIG. 5.

At 620, a three-dimensional representation of a polyp candidate is received. At 630 a viewpoint for the polyp candidate is chosen. For example, the entropy maximization techniques as described herein can be applied to select the viewpoint for a virtual camera.

At 640, a two-dimensional projection image is generated for the polyp candidate via the selected viewpoint.

Although not shown, any of the virtual lighting techniques described herein can also be applied when generating the two-dimensional representation.

Example 12

Exemplary Two-Dimensional Representation Generation Techniques

In any of the examples herein a two-dimensional representation can be generated via any of the projection technologies described herein. For example, a virtual camera viewpoint position can be chosen from which a projection image is generated, virtual lighting can be applied, or both.

Example 13

Exemplary System Configured to Extract Image Features

Figure 7:
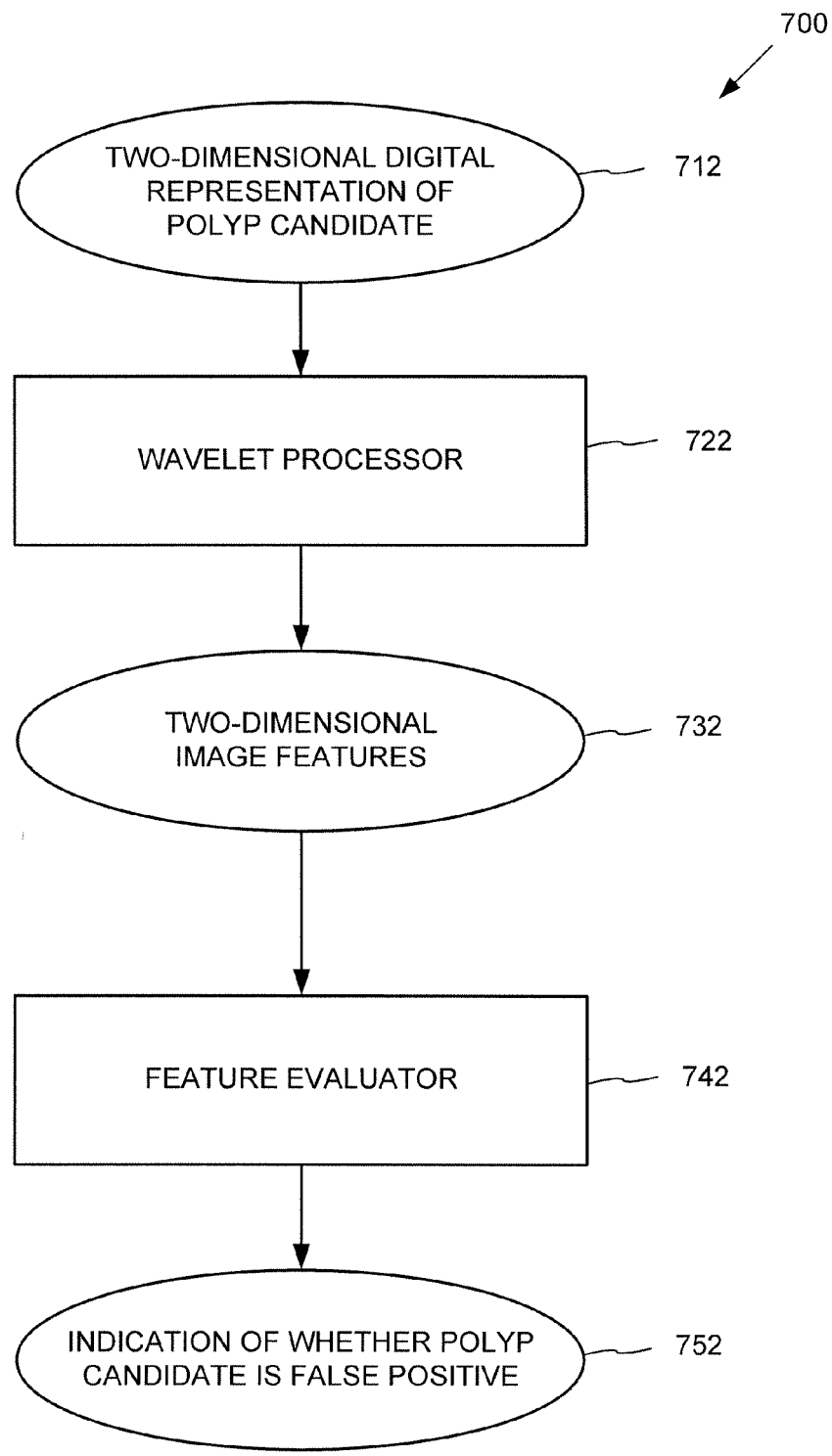
FIG. 7 is a block diagram of an exemplary system configured to extract two-dimensional image features from a two-dimensional digital representation of a polyp candidate and provide an indication of whether the polyp candidate is a false positive.

FIG. 7 is a block diagram of an exemplary system 700 configured to extract two-dimensional image features 732 from a two-dimensional digital representation 712 of a polyp candidate and provide an indication 752 of whether the polyp candidate is a polyp.

In the example, the system 700 accepts a two-dimensional digital representation 712 for a polyp candidate. The two-dimensional digital representation 712 can be any of the two-dimensional representations described herein. A wavelet processor 722 is configured to process the two-dimensional representation 712 and generate two-dimensional image features 732. For example, any of the wavelet-based features can be generated.

A feature evaluator 742 can process the image features 732 and output an indication 752 of whether the polyp candidate is a polyp.

Example 14

Exemplary Method of Extracting Image Features

Figure 8:
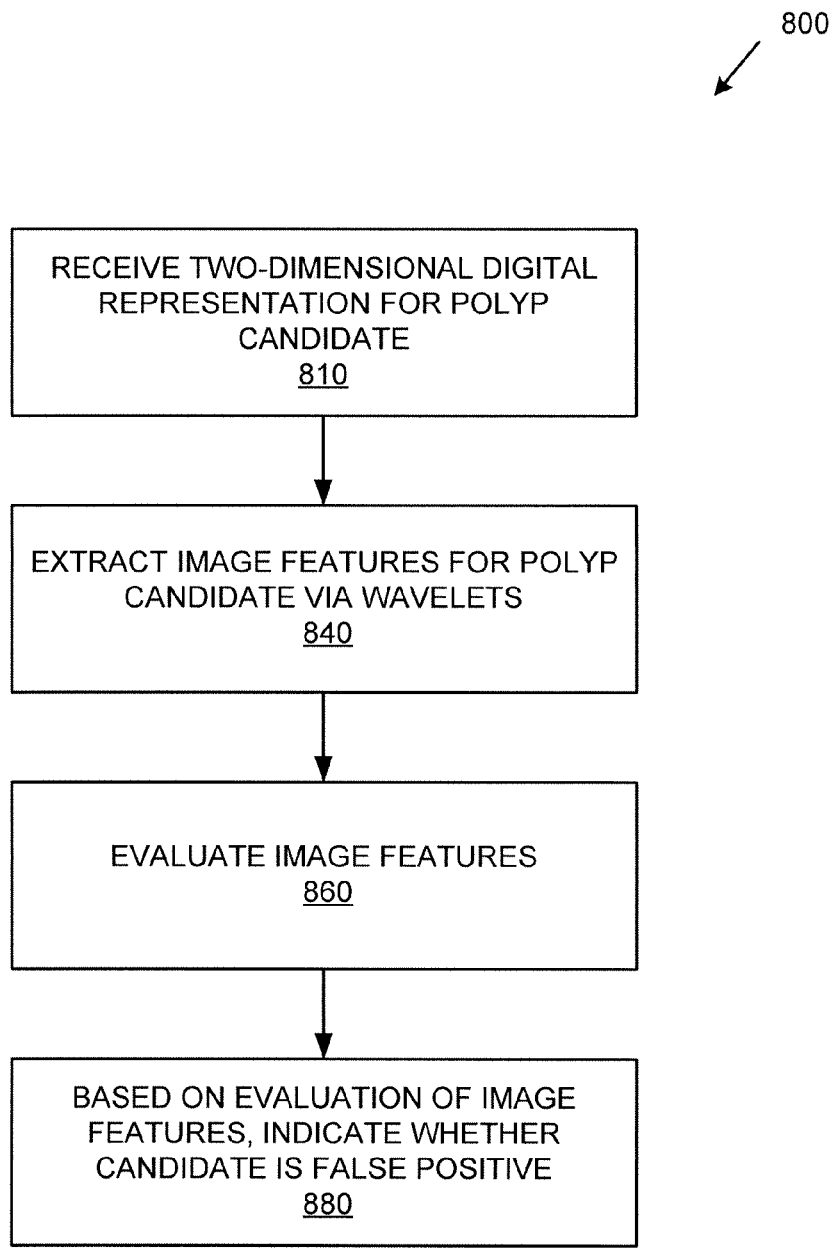
FIG. 8 is a flowchart of an exemplary method of generating image features for a polyp candidate and indicating whether the polyp candidate is a false positive.

FIG. 8 is a flowchart of an exemplary method 800 of extracting image features for a polyp candidate and indicating whether the polyp candidate is a false positive. The method 800 can be implemented, for example, by a system such as that shown in FIG. 7.

At 810, a two-dimensional representation for the polyp candidate is received. At 840, image features are extracted for the polyp candidate via any of the wavelet technologies described herein.

At 860, the image features are evaluated. At 880, based on the evaluation of the image features, it is indicated whether the polyp candidate is a polyp.

Example 15

Exemplary System Configured to Perform CT Colonography

Figure 9:
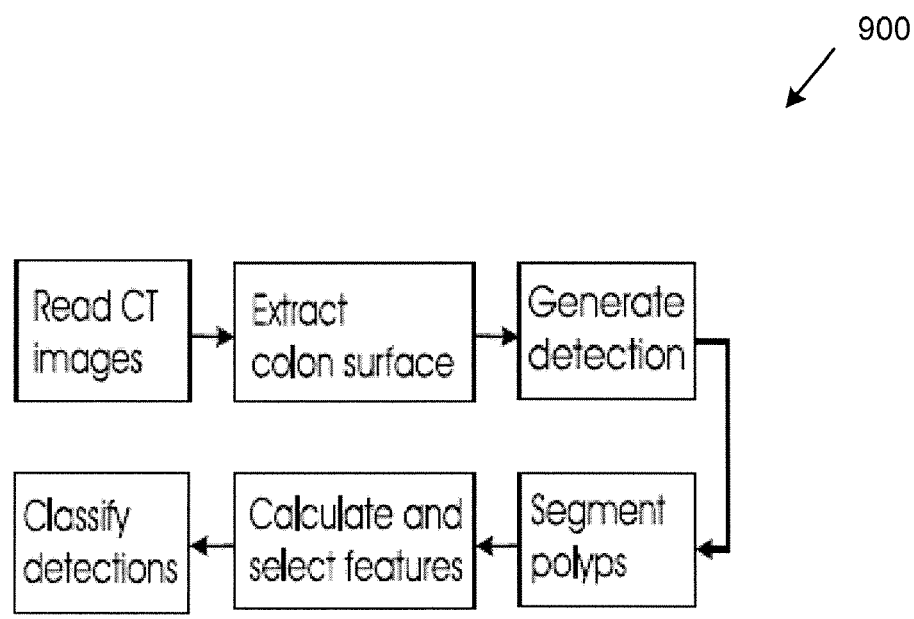
FIG. 9 is a block diagram of an exemplary system for performing CT colonography computer-aided detection.

FIG. 9 is a block diagram of an exemplary system 900 configured to perform CT colonography computer-aided detection and can be used in any of the examples herein. The system can identify polyp candidates based on geometric features of the colon surface and volumetric properties of the polyp candidates. In the example, imaging (e.g., CT) images are read, and the colon surface is extracted. For example, the CTC CAD system can segment the colon using a region growing algorithm and then extract the colon surface by an iso-surface technique.

For vertices on the colon surface, geometric and curvature features can be calculated and applied as a filter, and the regions of interest (polyp candidates) are then clustered based on connectivity along the filtered colonic surface.

One or more polyp candidates are segmented. For example, a knowledge-based polyp segmentation can be performed on the three-dimensional volume data, starting form the identified surface region. Features for the candidates are calculated and selected, and the candidates are classified. The resulting output is a set of one or more polyp candidates that can be processed by any of the technologies described herein. Such processing is sometimes called "post-processing" because it takes place after a preliminary determination regarding the polyp candidates has been made.

A virtual anatomical structure can be constructed to correspond to an anatomical structure represented in the digital representation. The software described herein can employ any combination of the technologies described herein. The digital representation can be derived from any technology that takes an image of an anatomical structure and turns it into a digital representation.

Figure 10:
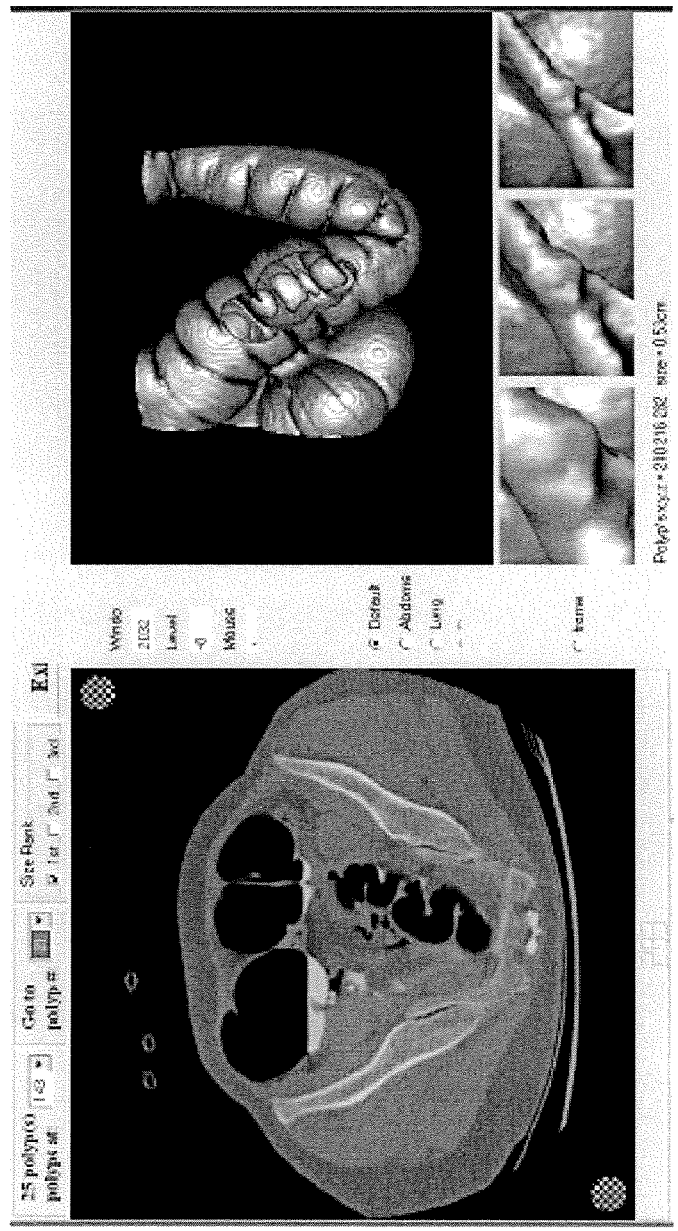
FIG. 10 is a Computed-Tomography-Colonography-Computer-Aided-Detection (CTCCAD) display window.

FIG. 10 is an exemplary display window that can be displayed as a user interface for a Computed-Tomography-Colonography-Computer-Aided-Detection (CTCCAD) system. In the example, the location of the polyp candidate is indicated via numerical x,y,z coordinates as well as being displayed visually.

Example 16

Exemplary Entropy Maximization Techniques

In any of the examples herein, a viewpoint for generating a two-dimensional projection image of a polyp candidate can be selected via an entropy maximization technique. Although such an approach sometimes describes "maximizing" entropy, the maximum possible entropy need not be found. Instead, any technique which chooses a higher entropy between or among alternatives can be used.

Example 17

Exemplary Error Minimization Techniques

In some of the examples herein, error minimization techniques are described. Although such an approach sometimes describes "minimizing" error, the minimum possible error need not be found. Instead, any technique that chooses a lower error between or among alternatives can be used.

Example 18

Exemplary Projection Image

Figure 11:
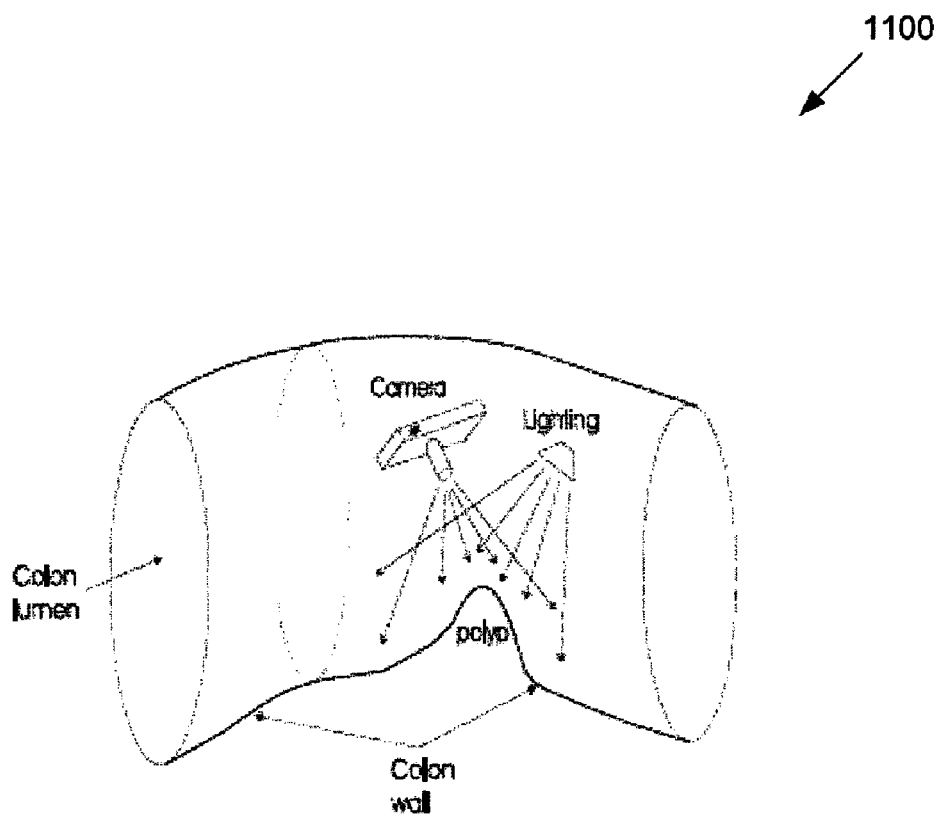
FIG. 11 is an illustration of generating projection images for polyp detections.

FIG. 11 is an illustration 1100 of generating a projection image for polyp detections via a snapshot technique. In the example, a projection image is generated by using a virtual camera inside the colon lumen and pointed at the colon wall toward the polyp candidate. The projection image is a snapshot taken by the virtual camera.

Figure 12:
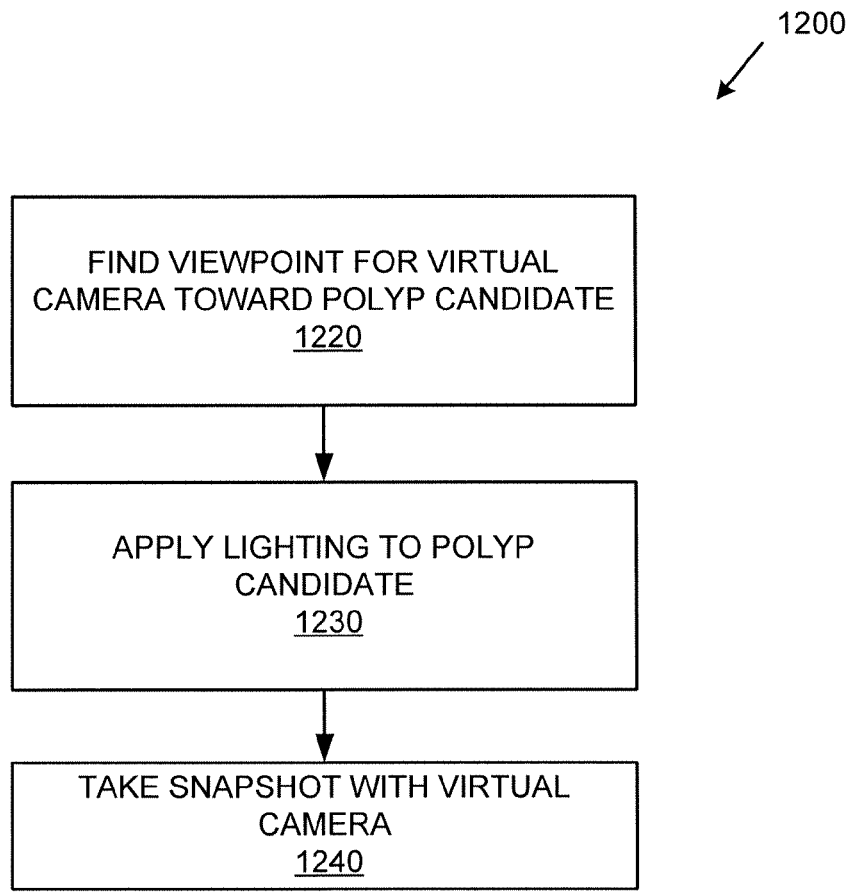
FIG. 12 is a flowchart of an exemplary method of generating a projection image for a polyp candidate.

FIG. 12 is a flowchart of an exemplary method 1200 of generating a projection image for a polyp candidate. At 1220, a viewpoint for a virtual camera pointed toward the polyp candidate is found. For example, the viewpoint entropy maximization techniques described herein can be used.

At 1230, virtual lighting is applied to the polyp candidate.

At 1240, a snapshot of the polyp candidate is taken with the virtual camera. The camera and lighting source locations can be adjusted via polyp surface information maximization techniques.

As a result, a two-dimensional representation of the polyp candidate (e.g., a two-dimensional endoluminal image) is produced as output.

Example 19

Exemplary Viewpoint Entropy

Figure 13:
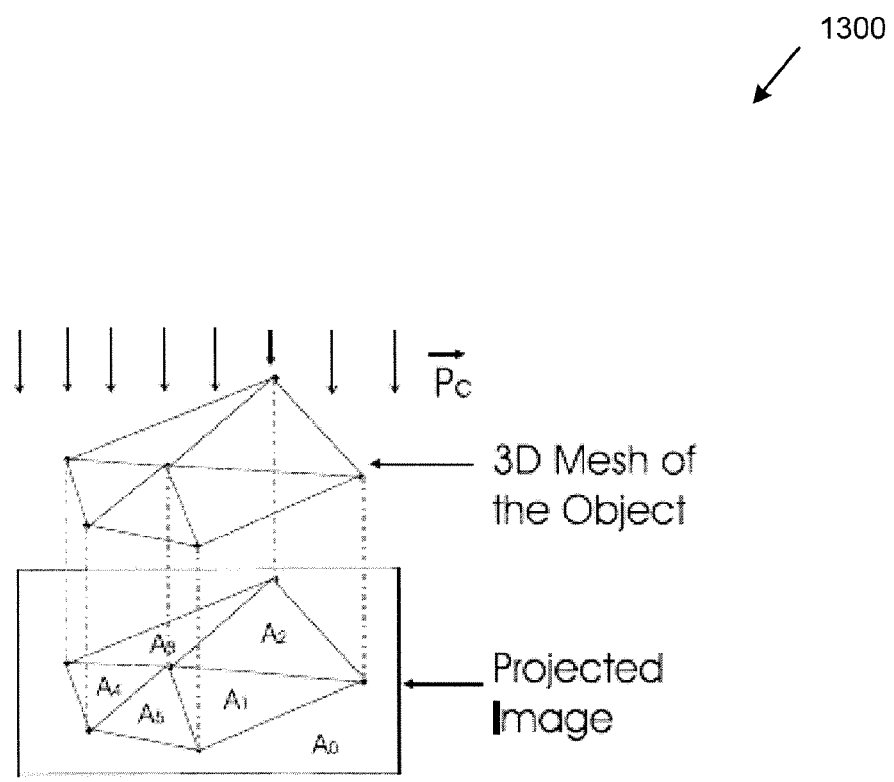
FIG. 13 is an illustration of viewpoint entropy for an object with a three-dimensional mesh representation.

FIG. 13 is an illustration 1300 of viewpoint entropy for an object (e.g., polyp candidate) with a three-dimensional mesh representation. In the example, a two-dimensional projected image is generated from a three-dimensional mesh of the polyp candidate. The projected image is the projection result of the three-dimensional mesh under the specified projection direction PC. Viewpoint entropy can be the amount of information that is contained in a two-dimensional projection image for a polyp candidate surface.

Figure 14:
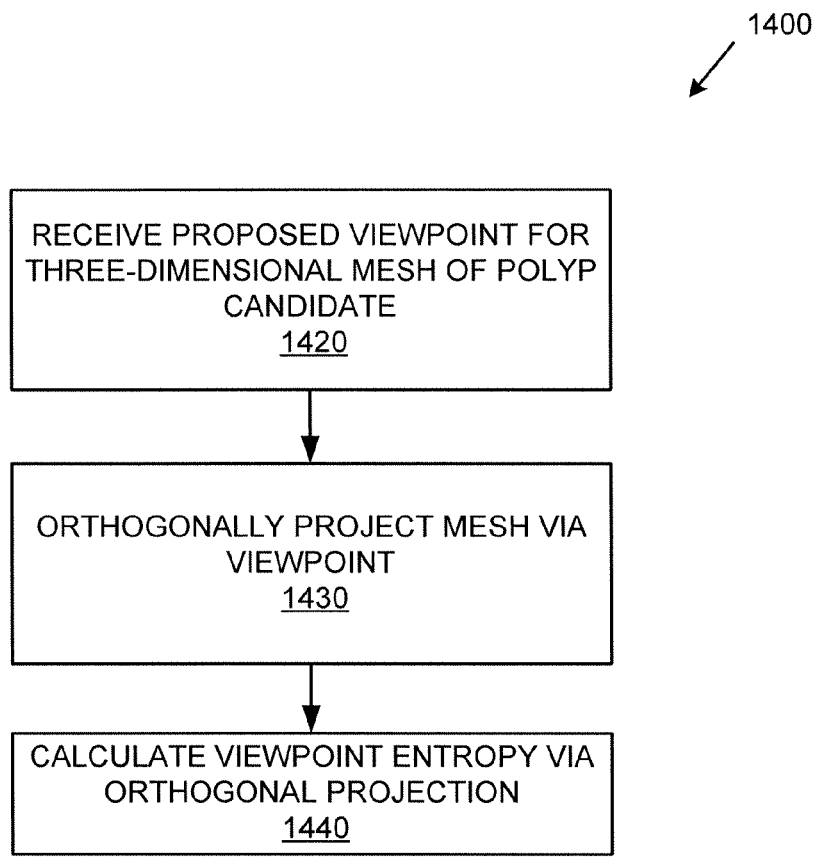
FIG. 14 is a flowchart of an exemplary method of calculating viewpoint entropy for a viewpoint.

FIG. 14 is a flowchart of an exemplary method 1400 of calculating viewpoint entropy for a viewpoint. At 1420, a proposed viewpoint for a three-dimensional mesh of a polyp candidate is received. At 1430, the mesh is orthogonally projected to an orthogonal projection via the viewpoint onto a two-dimensional plane.

At 1440, the viewpoint entropy is calculated via the orthogonal projection.

Alternatively, as described in Example 22, viewpoint entropy can be calculated without actually projecting the mesh into a two-dimensional plane.

The viewpoint entropy can be used to determine whether the proposed viewpoint is superior to another proposed viewpoint (e.g., by comparing viewpoint entropies and choosing the viewpoint with greater viewpoint entropy).

Example 20

Exemplary Viewpoint Selection: Centerline

In any of the examples herein, a viewpoint for generating a two-dimensional projection image of a polyp candidate can be selected from a location along a centerline of a virtual colon in which the polyp candidate resides.

Techniques for determining a centerline are described in Iordanescu and R. M. Summers, "Automated centerline for computed tomography colonography," Academic Radiol., vol. 10, pp. 1291-1301, 2003, which is hereby incorporated herein by reference and Van Uitert et al., "Subvoxel precise skeletons of volumetric data based on fast marching methods," Med. Phys. 34 (2), pp. 627-638, February 2007, which is hereby incorporated herein by reference.

Example 21

Exemplary Viewpoint Selection: Centerline with Coarse and Fine Searches

Figure 15:
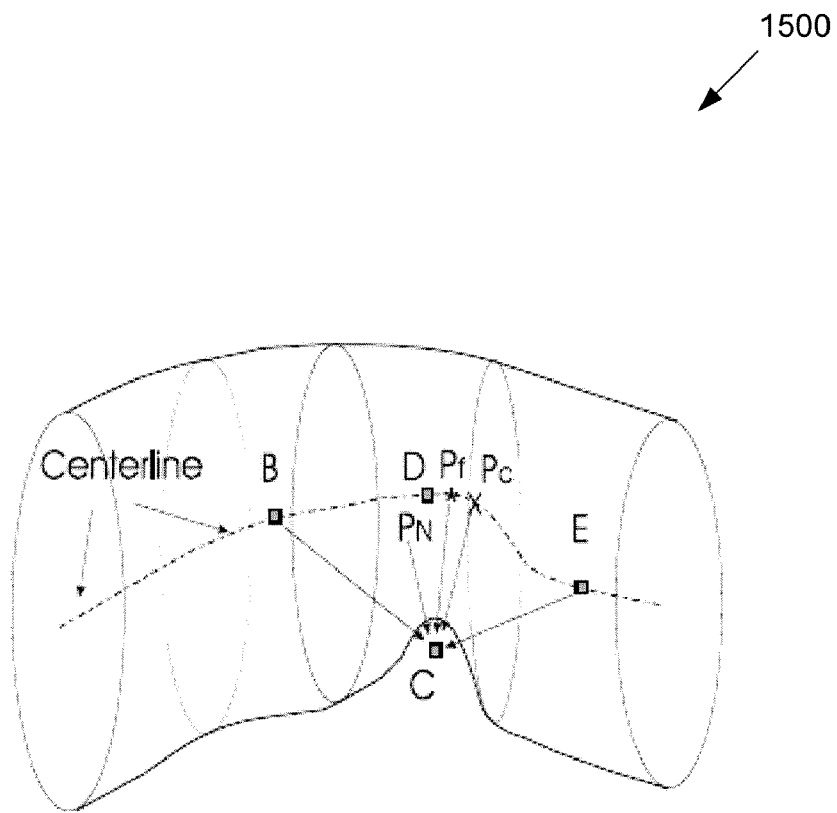
FIG. 15 is an illustration of finding a viewpoint for a projection image of a polyp candidate.

FIG. 15 is an illustration 1500 of finding a viewpoint for a projection image of a polyp candidate. A search path efficiently locates a good viewpoint. The dotted line represents the colon centerline. C is the polyp candidate's centroid. D is the nearest centerline point to C, and $P_N$ is the average normal of the polyp candidate surface.

If desired, a coarse search can first be performed between B and E to find a point $P_c$. Subsequently, a higher resolution search can be performed on points near $P_c$ to find $P_f$.

Figure 16:
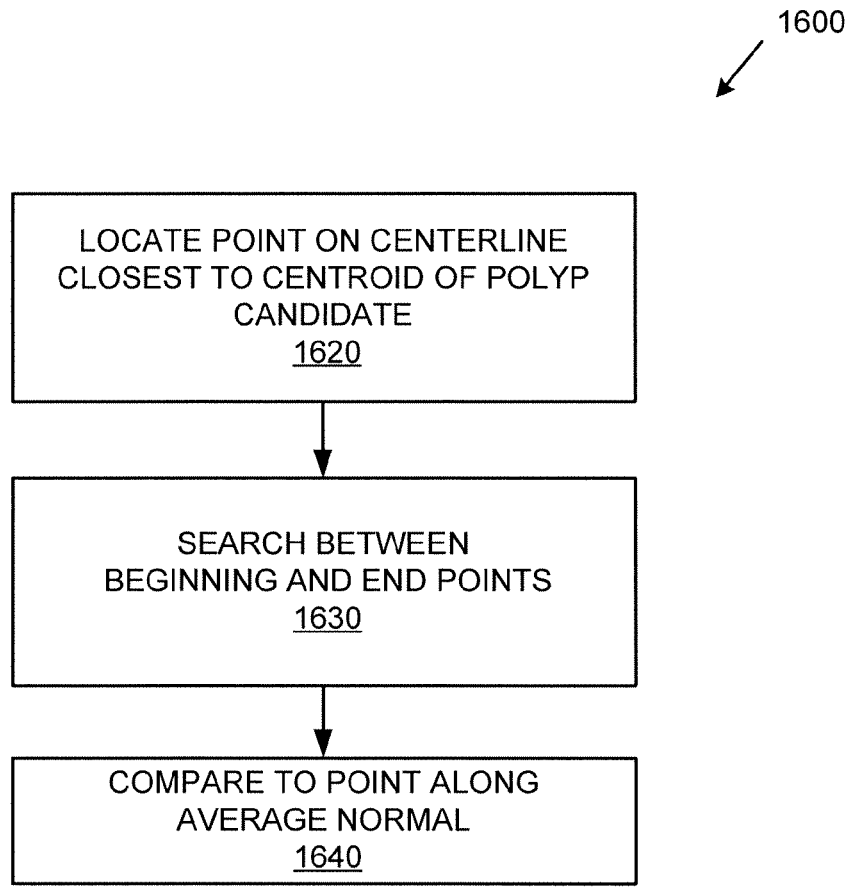
FIG. 16 is a flowchart of an exemplary method of finding a viewpoint for a projection image of a polyp candidate.

FIG. 16 is a flowchart of an exemplary method 1600 of finding a viewpoint for a projection image of a polyp candidate. At 1620 the point D on the centerline of the virtual colon closest to the centroid of the polyp candidate is located. At 1630, from D, beginning B and end points E on the centerline are found (e.g., by going a certain distance such as ±5 cm from D). The best point between B and E on the centerline is chosen (e.g., using a particular resolution or via coarse and fine searching) by a viewpoint entropy maximization technique.

At 1640, the point determined can then be compared to the point at a unit distance from the polyp candidate along the average normal from the candidate. The point with superior viewpoint entropy can be chosen as the viewpoint for the two-dimensional projection of the polyp candidate.

Example 22

Exemplary Viewpoint Entropy Calculation Directly From Mesh

Figure 17:
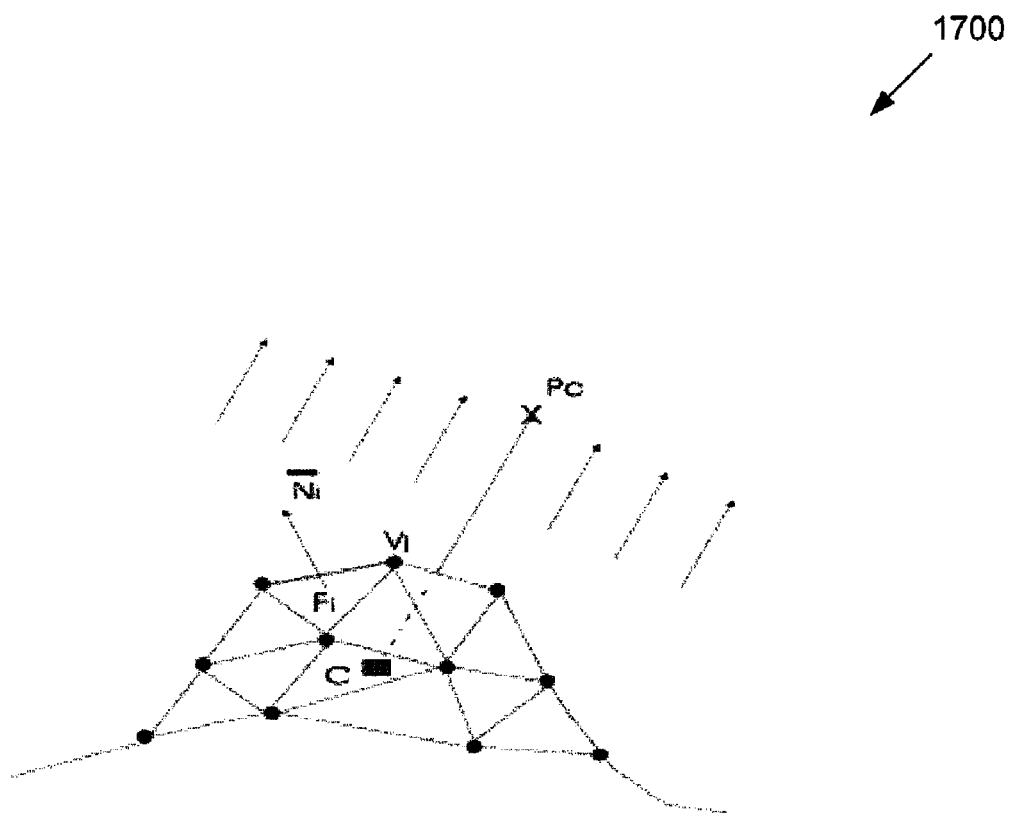
FIG. 17 is an illustration of calculating viewpoint entropy via a viewpoint.

FIG. 17 is an illustration of calculating viewpoint entropy via a viewpoint directly from a mesh of a polyp candidate. In the example, C is the centroid of the polyp candidate. $P_c$ is a viewpoint which determines the projection direction, $V_i$ represents one vertex on the mesh, and $F_i$ is one face in the mesh. Ni is a normal for a face.

Figure 18:
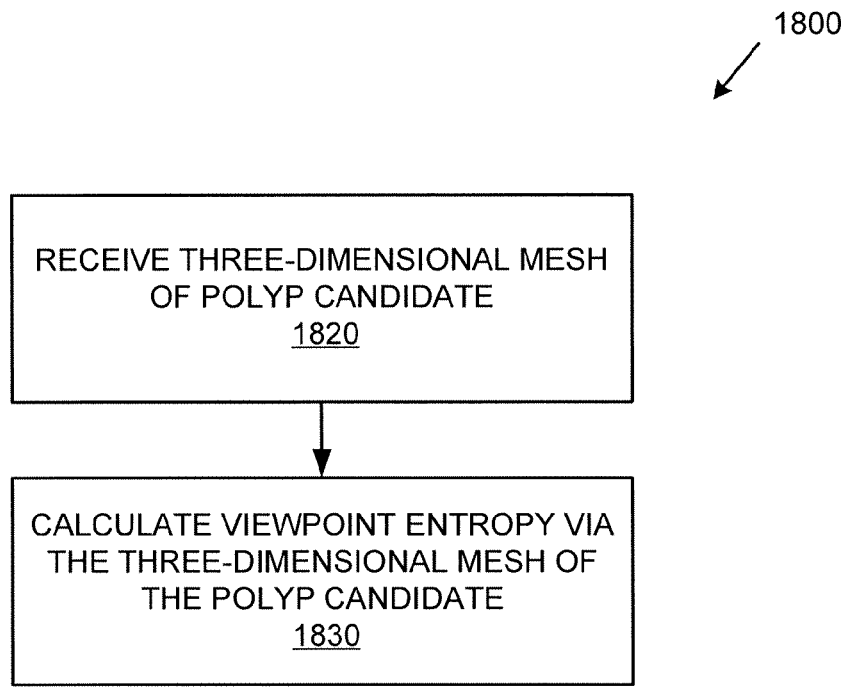
FIG. 18 is a flowchart of an exemplary method of calculating viewpoint entropy via a viewpoint directly from a mesh.

FIG. 18 is a flowchart of an exemplary method 1800 of calculating viewpoint entropy via a viewpoint directly from a mesh. At 1800, a three-dimensional mesh of the polyp candidate is received as input. At 1830, viewpoint entropy is calculated directly from the mesh (e.g., without projecting the three-dimensional mesh into a two-dimensional plane).

The face area and face normal can be determined from the mesh, so the areas for the respective faces, if they were projected, can be calculated. Thus, the viewpoint entropy can be calculated without actually projecting the three-dimensional mesh into a two-dimensional plane.

The viewpoint entropy calculation can be restricted to considering only the three-dimensional mesh of the polyp candidate. Thus, background information around the polyp candidate can be avoided during viewpoint selection.

Example 23

Exemplary Method of Generating Projection Image

Figure 19:
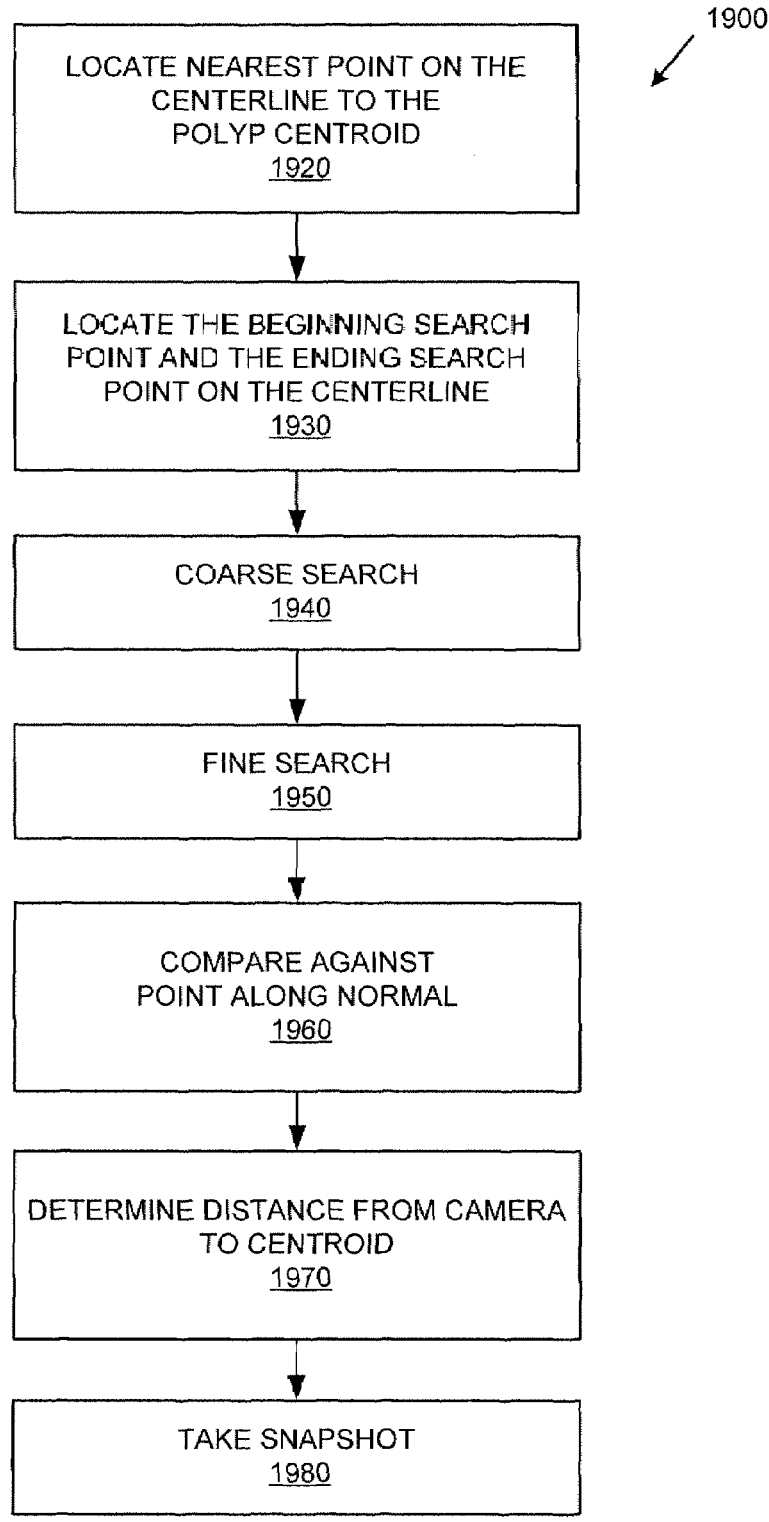
FIG. 19 is a flowchart of an exemplary method of generating a projection image of a polyp candidate.

FIG. 19 is a flowchart of an exemplary method 1900 of generating a projection image of a polyp candidate that can be used in any of the examples herein. At 1920, the nearest point, D, on the centerline to the polyp centroid, C, is located.

At 1930, the beginning search point B and the ending search point E are located on the centerline.

At 1940, a coarse search is performed. Te best viewpoint $P_c$ is found by evaluating the viewpoint entropy every n (e.g., 5) points between B and E and choosing the one having maximum entropy.

At 1950, a fine search is performed. The best viewpoint $P_c$ to $P_f$ is found by evaluating the viewpoint entropy of each of the n (e.g., 4) points left and right of the point $P_c$ and choosing the one having maximum entropy.

At 1960, the viewpoint entropy of point $P_N$ is evaluated, where $P_N$ is aligned to the average normal of the polyp detection with a unit distance. The point selected by the fine search $P_f$ is compared against $P_N$. If $P_N$ is a better viewpoint than $P_f$ (e.g., as indicated by viewpoint entropy), $P_N$ is chosen as the selected viewpoint.

At 1970, the distance from the virtual camera to the centroid is determined.

At 1980, a snapshot is taken for the polyp candidate.

Example 24

Exemplary Anatomical Structures

Although many of the examples herein describe a colon, the technologies can also be applied to any of the other anatomical structures described herein.

Example 25

Exemplary Anomalies of Interest

Any of the examples herein describing polyp candidates can be applied to anomalies of interest. Exemplary anomalies of interest include noncancerous growths, precancerous growths, and cancerous growths. Such anomalies include polyps, which are growths associated with mucus membranes and epithelial linings. Polyps of interest include colonic, small intestine, nasal, urinary tract, and uterine polyps. Other exemplary anomalies of interest includes instances of hyperplasia: an abnormal growth of the lining of an organ.

It is important that polyps and other anomalies be detected because they are often premalignant and if detected can be prophylactically removed to avoid development of diseases such as gastrointestinal adenocarcinoma. Thus, early detection enables early treatment (such as removal of the polyp) of possibly life-threatening conditions. In any of the examples herein, any of the generated images can be analyzed to detect anomalies of interest which correspond to anomalies of interest in the represented real world anatomical structure. Various software filtering mechanisms as described herein can be used on an initial list of detected anomalies of interest (e.g., polyp candidates) to provide a resulting list of anomalies of interest (e.g., confirmed candidates).

Example 26

Exemplary Wavelet Implementations

In any of the examples described herein, any wavelet analysis technology (e.g., those described herein) can be applied to the two-dimensional images (e.g., two-dimensional projection images) to determine whether the two-dimensional image depicts a polyp. For example, based on wavelet-based features extracted from the two-dimensional image, an indication can be given of whether the polyp candidate is a polyp.

Example 27

Exemplary Wavelet Technologies

In any of the examples herein, the technologies described as using wavelets can use any of a variety of wavelet analysis technologies. For example, wavelets with compact support, Daubechies wavelets, symmetrical wavelets, discontinuous wavelets, orthogonal wavelets, piecewise linear wavelets, scale-invariant wavelets, rotation-invariant wavelets, or the like.

Some of the examples described herein use Haar wavelets, which are discontinuous wavelets, but alternatives can be used instead.

Example 28

Exemplary Wavelet-based Features

In any of the examples herein, wavelet-based features can include wavelet coefficients at one or more orientations (e.g., in the vertical, horizontal, and diagonal directions, or combinations thereof) at one or more levels (e.g., levels 1-5 or the like). Wavelet decomposition can split the frequency space into multiple scales and orientations. Features can be extracted from the wavelet coefficients. In addition, other features such as energy and entropy can be used. Predictive neighbors can also be used to determine prediction coefficients, which can be used as features. Features can also be calculated from predictive errors.

Mean, variance, skewness, kurtosis, or combinations thereof can be extracted.

Energy and entropy can also be extracted for one or more orientations at one or more levels.

Haar wavelet coefficients can be used.

Example 29

Exemplary Wavelet-based Feature Extraction

In any of the examples herein, wavelet features can include wavelet predictive error features. Wavelet predictive error features can be extracted via searching for most predictive neighbor coefficients of wavelet coefficients. The predictive error can be extracted as a wavelet-based feature. Mean, variance, skewness, and kurtosis for the errors can also be extracted (e.g., for one or more levels).

A piecewise linear orthonormal floating search technique can be used to search most predictive neighbors.

Example 30

Exemplary Wavelet-based Feature Selection

In any of the examples herein, features can be selected in a variety of ways. For example, a group of m features can be selected. Proposed replacement features can be substituted only if they improve the fitness value.

Example 31

Exemplary Classifier

A classifier for evaluating the wavelet-based features can be configured to indicate whether the polyp candidate is a polyp. For example, a plurality of support vector machines (e.g., in a committee arrangement) can be configured to receive a plurality of wavelet-based features for a two-dimensional snapshot of the polyp candidate. Outputs can be combined (e.g., via averaging or the like) by a module to indicate whether the support vector machines as a whole indicate whether the polyp candidate is a polyp.

The classifier can be trained via wavelet-based features for two-dimensional projection images of known true positive polyps and known false positive polyp candidates.

The support vector machines can take different features as input. For example, a first support vector machine can be trained via a first set of wavelet-based features, and a second support vector machine in the group can be trained via a second set of wavelet-based features different from the first set.

Example 32

Exemplary CTCCAD Detection Examples

Figure 20:
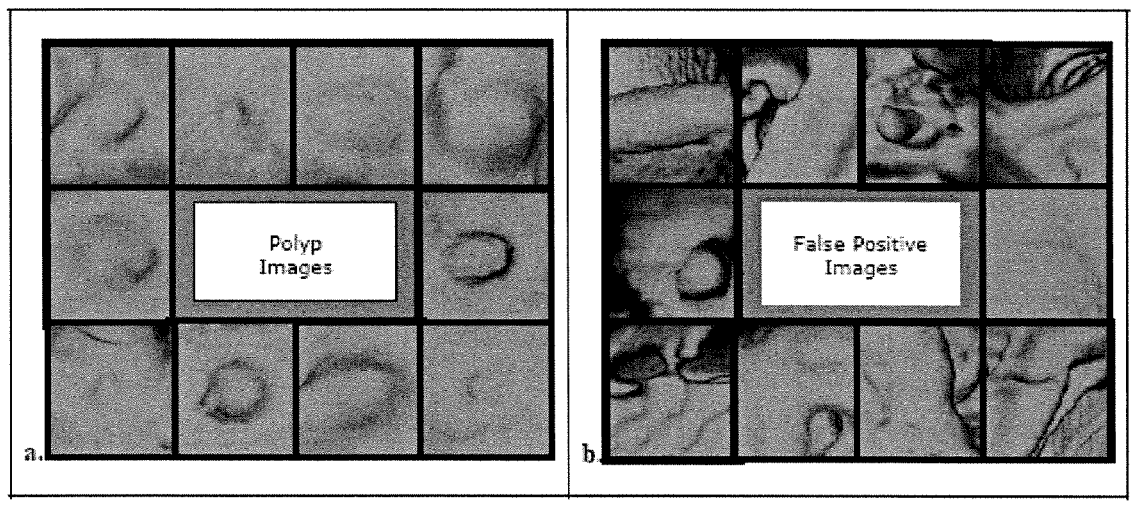
FIGS. 20A-B show exemplary two-dimensional images of identified polyp candidates.

FIGS. 20A-B show exemplary two-dimensional images of polyp candidates identified by a first phase CTCCAD detection. Such two-dimensional images can be analyzed via any of the technologies described herein to determine whether the polyp candidate is a polyp.

Example 33

Exemplary Implementations

Although the number of possible approaches to implementing the technologies described herein are limitless, various implementations were implemented and tested. Implementation A draws on wavelet technologies described by Lyu, "A Digital Technique for Art Authentication," *PNAS*, vol. 101, no. 49, pp. 17006-10, Dec. 7, 2004 ("Lyu"). Implementation B extends some of the technologies further and can use alternatives. Both can incorporate any of the features described herein to go beyond those described in Lyu.

Example 34

Exemplary Implementation A

In an implementation, 26 virtual colonoscopy cases were obtained, each containing at least one known polyp, whose position was previously determined by optical colonoscopy. The cases were picked at random from a database consisting of the supine scans of patients with 6-9 mm polyps not under fluid. Cases were run through an existing CTCCAD program, such as that depicted in FIGS. 9 and 10. The program scans the colon and returns a list of detections (e.g., polyp candidates) with corresponding images.

A screen capture tool was used to save a bitmap image of the en face endoluminal view of each detection. The images were 192×222 pixels, plus or minus one pixel. For each case, one true polyp (e.g., chosen from FIG. 20A) and one false positive detection (e.g., chosen from FIG. 20B) were used.

Figure 21:
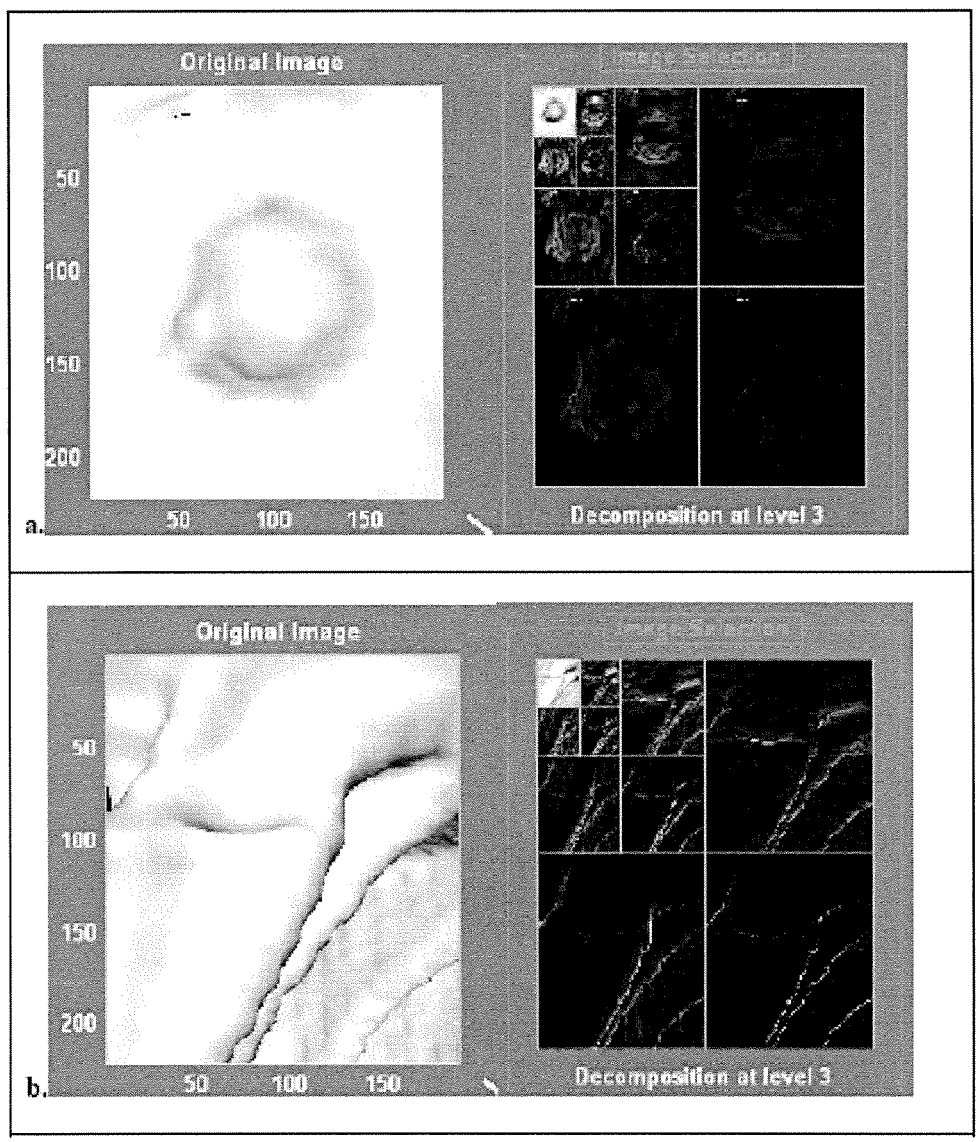
FIGS. 21A-B are MATLAB visualizations of wavelet decompositions.

The 52 bitmap images were then converted to grayscale and analyzed using MATLAB version 6.5's wavelet toolbox. A 2D discrete wavelet decomposition was performed using the Haar wavelet basis at levels 1-5 in the horizontal, vertical, and diagonal directions which resulted in 16 subband coefficients for each image. FIGS. 21A-B are MATLAB visualizations of wavelet decompositions and show one example of the wavelet transformation performed at levels 1-3. FIG. 21A shows wavelet-based data for a polyp (e.g., as verified by a human classifier) and FIG. 21B shows wavelet-based data for a false positive (e.g., as determined by a human classifier).

The wavelet decomposition of an image yielded a set of wavelet coefficients which describe both the large and small-scale shape features of the surface. Drawing on a technique described in Lyu, four descriptive statistics were computed at 1-3 levels for each orientation from these coefficients: mean, variance, skew, and kurtosis. Then, a linear predictor function was used to compute the second order error statistics for each coefficient subband at levels 1-3, based on the linear prediction error of each coefficient, in the subband by its spatial, orientation, and scale neighbors. First, the 7 numerically closest coefficient neighbors were found iteratively from among its 80 neighbors. For example, at a vertical orientation at scale i, the neighbors of coefficient Vi(x,y) were defined as:

$$V_i(x-c_x, y-c_y), H_i(x-c_x, y-c_y), D_i(x-c_x, y-c_y),$$
$$V_{i+1}\left(\frac{x}{2}-c_x, \frac{y}{2}-c_y\right), H_{i+1}\left(\frac{x}{2}-c_x, \frac{y}{2}-c_y\right), D_{i+1}\left(\frac{x}{2}-c_x, \frac{y}{2}-c_y\right),$$
$$V_{i+2}\left(\frac{x}{4}-c_x, \frac{y}{4}-c_y\right), H_{i+2}\left(\frac{x}{4}-c_x, \frac{y}{4}-c_y\right), D_{i+2}\left(\frac{x}{4}-c_x, \frac{y}{4}-c_y\right),$$
(1)

where cx={−1,0,1} and cy={−1,0,1}, and Vi(x,y) was excluded. Here Vi, Hi and Di denote the wavelet coefficients in the vertical, horizontal and diagonal directions at level i. The seven closest neighbors were determined by finding the minimum difference between these neighbors and the original coefficient, and repeating the process 6 times. Then, a column vector $\vec{V}$ was created containing the values of all original coefficients in the subband. A matrix Q was also created, composed of 7 columns of closest neighbor coefficients for the corresponding coefficient in the subband. Using the linear predictor $\vec{V}=Q\vec{w}$, a column of predictor coefficients $\vec{w}$ was computed by $$\vec{w}=(Q^T Q)^{-1} Q^T \vec{V}$$
(2)

The errors in the linear predictor were the residuals $$\vec{E}=(\vec{V}-Q\vec{w})^2$$
(3)

The same four statistics (mean, variance, skew, kurtosis) were computed for the subband and this process was repeated for respective subbands at levels 1-3. The feature extraction method in this can give a 72 feature vector for respective images.

Next, feature selection and training of a committee classifier were performed. Feature selection was done using a genetic algorithm. Ten-fold cross-validation training was done using a support vector machine (SVM) classifier, ultimately generating a 7 member SVM committee classifier using 4 features each.

Figure 22:
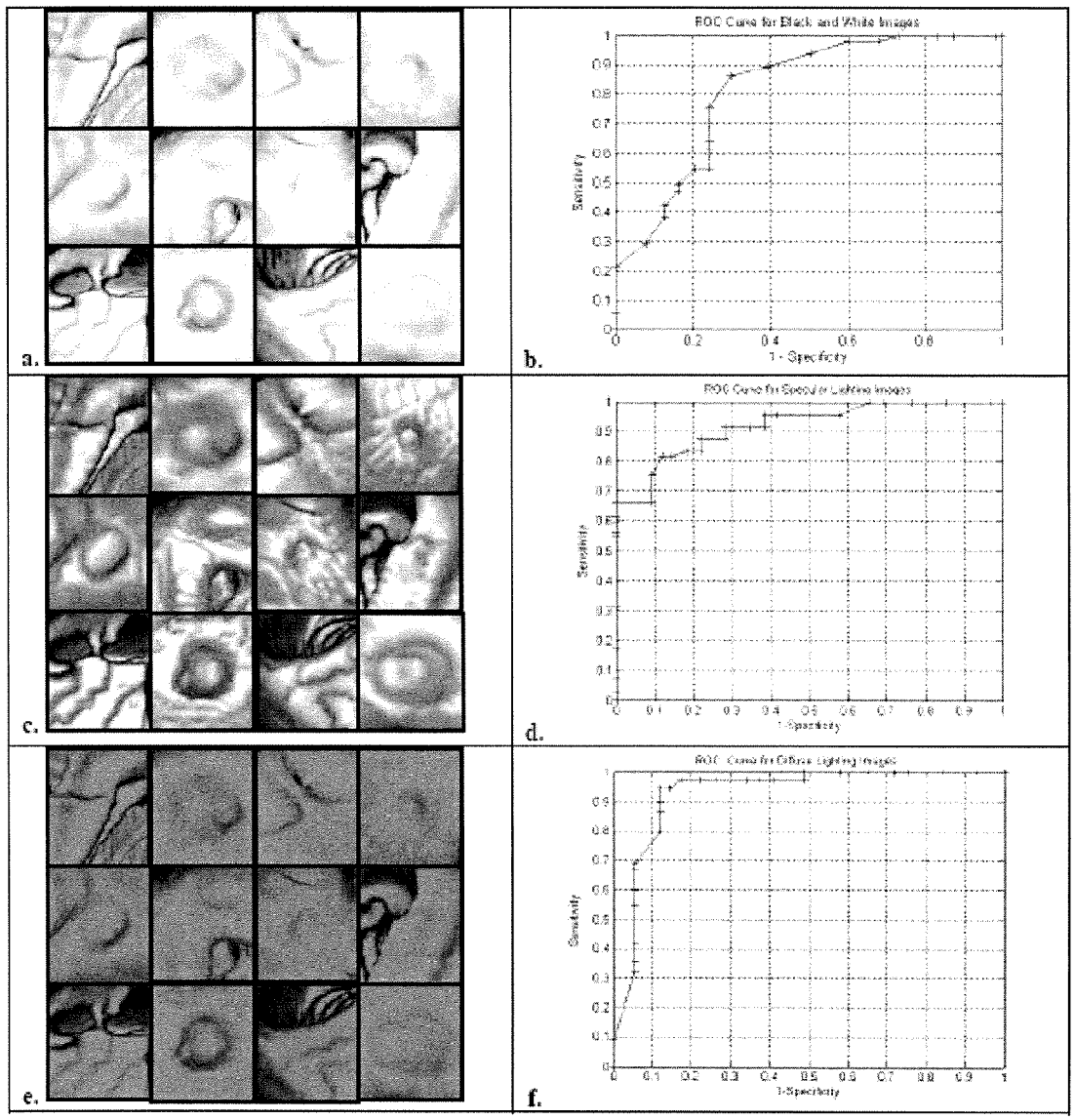
FIGS. 22A-F are mosaics of alternating polyp and false positive images.

This procedure was carried out on 3 sets of data, varying only in color scheme and lighting attributes, in order to determine which images were most compatible with a wavelet analysis. One data set contained black and white images (FIG. 22A). Another contained true color images with specular lighting added (FIG. 22C), and the third contained true color images with all except diffuse lighting removed (FIG. 22E). In the examples, the images in each pane A, C, and E alternate between false positive images and images of polyps.

The classifier produced a specificity reading for each data set, representing the percent of false positives that were correctly identified when the classifier was run at a sensitivity level allowing correct identification of all polyps. An average ROC curve from 10 bootstraps was also created to visualize these results, with mean area under the ROC curve (AUC) representative of the efficiency of the classifier for the particular data set.

Example 35

Exemplary Implementation A: Results

The following table shows the classifier results for the three data sets. The classifier performed the best with the diffuse lighting data, correctly identifying about ½ of the false positive detections at a sensitivity of 100%. Mean ROC curves for the data sets for FIGS. 22A, 22C, 22E are shown in FIGS. 22B, 22D, and 22F, respectively, and the mean area under the curve (AUC) as well as the standard deviation in this measurement are included in the table below. The results again support the conclusion that the diffuse lighting pictures are best suited to this type of analysis.

TABLE 1

| Data set | Sensitivity | Specificity | AUC | Stand. Dev. |
| --- | --- | --- | --- | --- |
| Black and white | 100% (27/27) | 26.8% (8/27) | 0.81 | 0.067 |
| Specular | 100% (26/26) | 34.5% (10/26) | 0.92 | 0.046 |
| Diffuse | 100% (26/26) | 51.4% (13/26) | 0.93 | 0.047 |

Upon reviewing the misclassified images, many of the incorrectly identified false positives were found to contain shapes similar to polyps, or contained no identifiable shapes at all. One case, present in the black and white data set, was left out of the specular and diffuse data sets due to an error in image processing.

Figure 23:
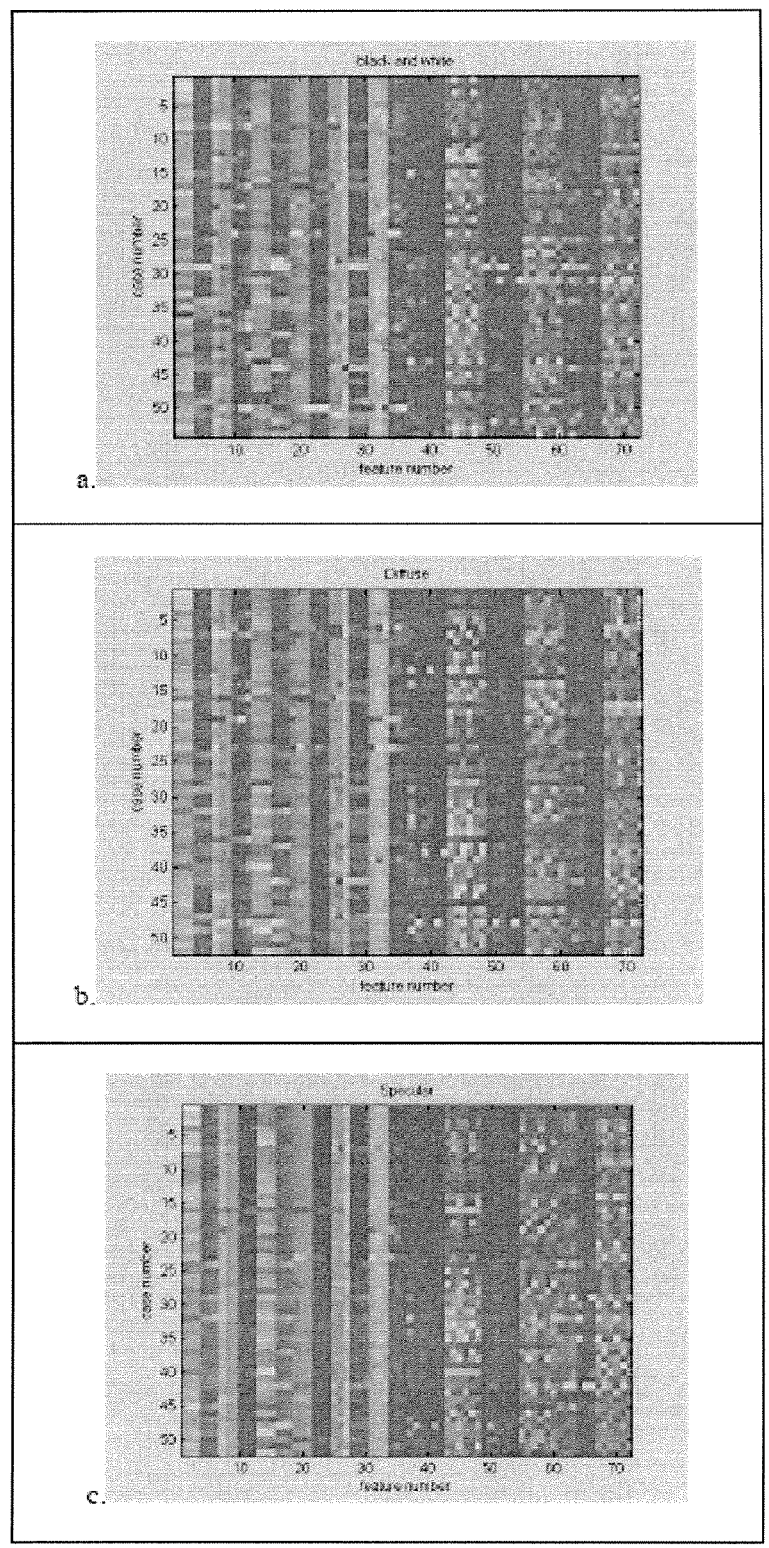
FIGS. 23A-C are graphic illustrations of wavelet statistics. Instead of green and yellow, the drawing shows darker and lighter, respectively.

FIGS. 23A-C are graphic illustrations of wavelet statistics for the data sets for FIGS. 22A, 22C, 22E, respectively. Originally in green and yellow, the drawing substitutes darker and lighter, respectively. Wavelet statistics for black and white (FIG. 23A), specular (FIG. 23B), and diffuse (FIG. 23C) data are shown. Green (shown as darker) represents lower values for the statistic, and yellow (shown as lighter) represents higher values. The top portion of the graphs are the true positives (i.e., case number 1-26), while the bottom portion of the graphs are the false positives (case numbers 27-52).

Example 36

Exemplary Implementation A: Conclusion

Ultimately the idea behind the wavelet analysis was to capture some of the information so readily apparent to the human eye, such as shape and contour, in a form that can be understood and manipulated by a computer. Since the wavelet analysis is dependent on the visual properties of an image, the detection images are modified to include full color and only diffuse lighting in order to produce the best classification. In these images, with minimal extraneous shadows and reflections and maximum range of shading, the human eye is best able to discern a polyp structure. The wavelet decomposition of virtual colonoscopy images is able to distinguish real polyps from many non-polyp CTCCAD detections, enabling exclusion of about one-half of the non-polyp detections. This technique can be added to the filtering process of the CTC-CAD program to aid the radiologist in expediting the CT reading process and can be useful in preventing unnecessary optical colonoscopies.

Example 37

Exemplary Wavelet Definition

Figure 24:
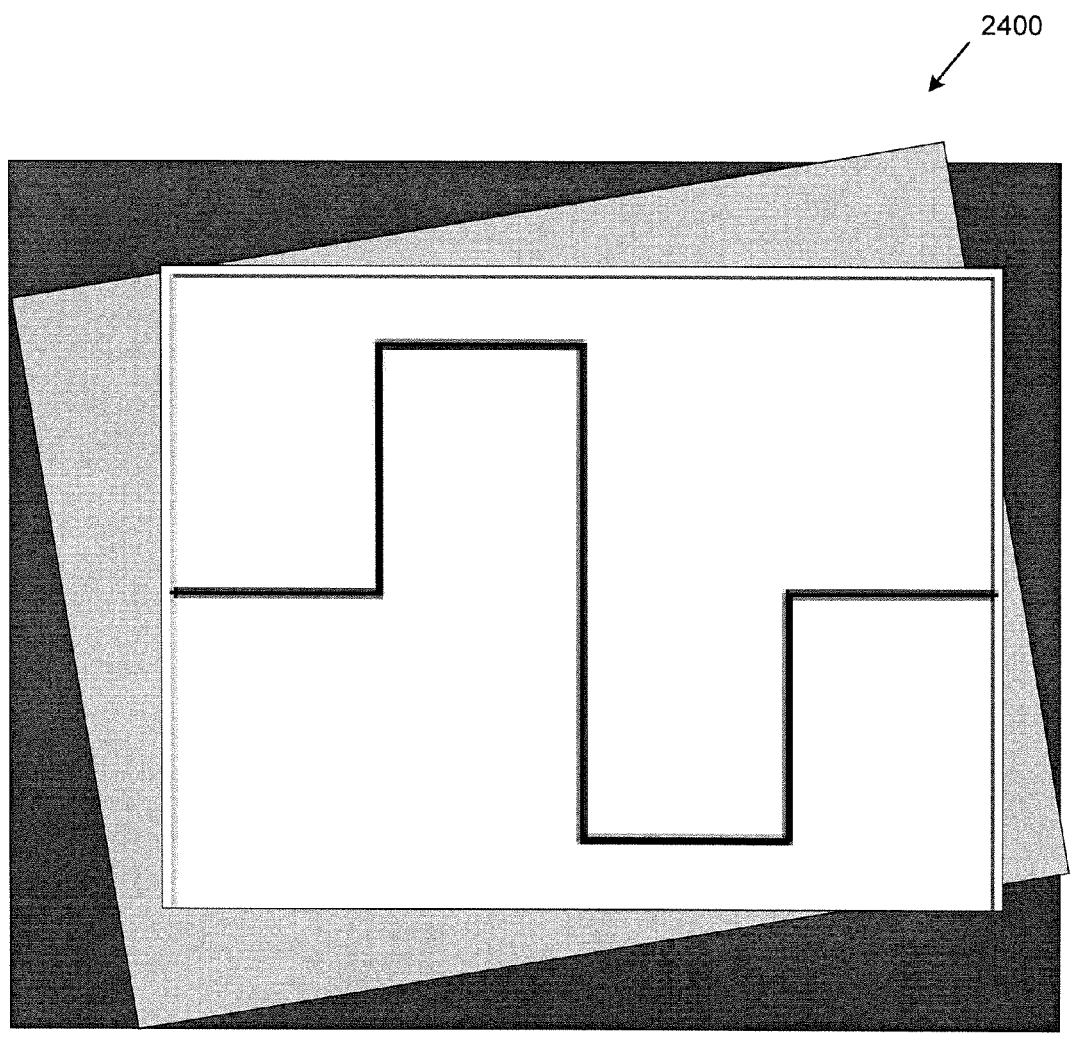
FIG. 24 is an illustration of a wavelet.

FIG. 24 is an illustration of an exemplary wavelet definition 2400 that can be used in any of the examples herein. In the example, a Haar wavelet definition 2400 is shown. Wavelets can be small oscillations with zero net area that are localized in time.

Example 38

Exemplary Mathematical Description of Wavelets

FIG. 25 is a mathematical description 2500 of wavelets. $h_0$ and $h_1$ can be coefficients of high and low filter banks. k can be a constant.

A general wavelet equation and a Haar wavelet equation are shown and can be used in any of the examples herein.

Example 39

Exemplary Wavelets

Wavelets can use a multi-scale, multi-orientation approach to describing signals and images by separating them into layers of detail and low-resolution approximations. A discrete wavelet analysis of an image can output wavelet coefficients in the horizontal, vertical, and diagonal directions at specified levels of analysis. Statistics gathered from the coefficients can provide a powerful tool in image comparison.

Example 40

Exemplary 2D Projection Images for Polyp Candidates

In any of the examples herein, a CT data set for a colon can be acquired. CTCCAD software can then segment the colon using a region growing algorithm, after which regions of interest (e.g., associated with respective polyp candidates) along the colon wall are identified. For the identified regions, the average coordinate and normal of vertices define a centroid and a unit vector, which can be used to set the position and orientation of a virtual camera. The virtual camera can then take a two-dimensional image for the identified region. The image can be a projection, snapshot, or the like.

The software can then repeat the above technique for respective identified regions and return a list of detections with corresponding images. The images can be save as inputs for wavelet analysis as described herein.

Example 41

Exemplary Implementation B: Technique

Techniques from Implementation A can be applied to the images obtained via the technique described in Example 40 in an implementation called "Implementation B." Wavelet decomposition can split the frequency space into multiple scales and orientations. $V_i(x,y)$, $H_i(x,y)$, and $D_i(x,y)$ can be used to denote the wavelet coefficients in the vertical, horizontal, and diagonal directions at level i. The wavelet decomposition can be first performed at levels 1-5 for the image to be studied, which yields a set of wavelet coefficients. Four statistics can be computed for each orientation at level 1-3 from the following coefficients: mean, variance, skew, and kurtosis, yielding 36 features for the image. Another 36 features can be calculated based on the concept that the magnitudes of subband coefficients are correlated to their spatial, orientation, and scale neighbors. The magnitude of one coefficient can be predicted by a set of its neighbors, i.e., $V_i(x,y)$ may be given by $$|V_i(x, y)| = \sum_{k=1}^{K} w_k |N_k(x_k, y_k)| \qquad (4)$$

where $w_k$ denotes scalar weights for the neighbor $N_k$, and $|\cdot|$ denotes magnitude. The K most predictive neighbors can be searched via brute-force in the following 80 neighbors to minimize the prediction error within each subband, $$V_i(x-c_x, y-c_y), H_i(x-c_x, y-c_y), D_i(x-c_x, y-c_y),$$
$$V_{i+1}\left(\frac{x}{2}-c_x, \frac{y}{2}-c_y\right), H_{i+1}\left(\frac{x}{2}-c_x, \frac{y}{2}-c_y\right), D_{i+1}\left(\frac{x}{2}-c_x, \frac{y}{2}-c_y\right)$$
$$V_{i+2}\left(\frac{x}{4}-c_x, \frac{y}{4}-c_y\right), H_{i+2}\left(\frac{x}{4}-c_x, \frac{y}{4}-c_y\right), D_{i+2}\left(\frac{x}{4}-c_x, \frac{y}{4}-c_y\right),$$

where $c_x=\{-1,0,1\}$ and $cy=\{-1,0,1\}$. Let the vector $\vec{V}$ contain the coefficient magnitudes of $V_i(x,y)$ strung out into a column vector. After finding the K most predictive neighbors, the predictive error can be calculated as $$E(\vec{w})=[\vec{V}-Q\vec{w}]^2. \qquad (5)$$

where matrix Q contains the chosen neighbors, and $\vec{w}$, was determined by a least square algorithm. An additional 36 features were then calculated for the errors, $E(\vec{w})$, including their mean, variance, skewness, and kurtosis for the subband at level 1-3.

Example 42

Exemplary Implementation C: Feature Extraction

Another implementation called "Implementation C" can use an orthonormal floating search (OFS) algorithm to find the 8 most predictive neighbors. Compared to a brute force search, the OFS can be computationally very efficient but can give a statistically similar result.

Energy and entropy features can be computed for each subband. For the vertical subband $V_i(x,y)$, for example, the following can be calculated:

$$energy_i = \frac{1}{M \times N} \sum_{x=1}^{M} \sum_{y=1}^{N} V_i^2(x, y), \qquad (6)$$

$$entropy_i = \frac{-1}{M \times N} \sum_{x=1}^{M} \sum_{y=1}^{N} \frac{V_i^2(x, y)}{D^2} \log \frac{V_i^2(x, y)}{D^2}, \qquad (7)$$

where $$D = \sum_{x=1}^{M} \sum_{y=1}^{N} V_i^2(x, y),$$

and M, N are dimensions of subband $V_i(x,y)$.

Mean, variance, skewness, and kurtosis for coefficients can be calculated at levels 4 and 5. Therefore, 150 features can be obtained in total for an image.

Example 43

Exemplary SVM Committee Classifier

In any of the examples herein, an SVM Committee Classifier can be used to classify a polyp candidate based on its wavelet-based features. Given a set of data pairs $\{x_p, i_p\}_{p=1}^{N}$, where $x_p \in R^N$ is the feature vector extracted from an image, and $i_p \in \{+1,-1\}$ is a class label (true polyp, true negative) associated with $x_p$, an SVM $$f(x)=w^T\phi(x)+b=0 \qquad (8)$$

defines a hyperplane to separate data points. Here w and b are the plane parameters, and $\phi(x)$ is a function mapping the vector x to a higher dimensional space. The hyperplane can be determined using a Structural Risk Minimization technique. A technique described in Platt, "Probabilistic Outputs for Support Vector Machines and Comparisons to Regularized Likelihood Methods," *Advances in Large Margin Classifiers*, MIT Press, 1999, can be used to transfer the SVM output, f(x), to a posterior probability (e.g., "score"). An SVM committee having a set of SVM's trained using different respective feature subsets can be used.

The overall score for a single candidate can be the average of the SVM's outputs. A threshold (e.g., 0.5) can be applied to the score. A true polyp is indicated if the score is greater than the threshold. Otherwise, the candidate is classified as negative (e.g., a false positive).

Example 44

Exemplary Selection of Feature Subset and Selection of Committee

In any of the examples herein, a wrapper type feature selection can be used, where an SVM classifier is utilized for fitness evaluation. The fitness value of a feature vector can be defined as the average of sensitivity and specificity of the involved SVM. First a group of 4 feature vectors can be randomly generated. Then one feature in the vector can be replaced with a new feature. If the substitution improves the fitness value, the new vector replaces the old one.

The process can be iterated on respective features in the vector until no further improvements are found. Such an approach can perform similarly to a genetic algorithm.

The feature selection algorithm can generate a large number of combinations of 4 features and report the 1000 having the highest ranked fitness values. The best SVM committee with 7 members can then be found among the 1000 combinations.

Example 45

Exemplary Validation: Implementation B and Implementation C

The feature extraction technique of Implementation C and the technique of Implementation B were compared on CTC data, based on three-fold cross-validation and receiver operating characteristic (ROC) analysis.

A CTC procedure was performed on 44 patients with a high suspicion of colonic polyps or masses. All patients had at least one polyp and each polyp was verified by follow-up optical colonoscopy. These patients were chosen from a larger cohort who underwent contrast-enhanced CTC. Selection criteria included patients having at least one polyp greater than 5 mm in diameter.

A majority of the polyps were identified on both the prone and supine views. In the study, only polyps with a size between 6 and 9 mm were of interest. The range is of particular importance because CAD has already been shown to have a high sensitivity and reasonable specificity for polyps of larger size (e.g., 10 mm and larger).

The CTC CAD software produced 42 true detection images for 6-9 mm polyps and 492 false positives for the 44 patients. Those 42 true detection images consisted of 28 unique polyps because one polyp might produce multiple detections. A two-dimensional wavelet decomposition using the Haar basis was then performed on each image, and Implementation B and Implementation C were applied. Finally, feature selection and SVM committee selection (i.e., as described in Examples 43 and 44) were performed.

The data sets contained 534 polyp candidates identified by the software. A three-fold cross-validation was used to characterize performance of Implementations B and C. In three-fold cross validation, each data set was first randomly divided into three equal-sized parts. One of the three parts was held out as a test set. The remaining two parts were used for feature and committee selection, which led to a trained SVM committee model. The model was then applied to the held-out set to obtain test results.

The training and testing procedures were repeated three times so that each part was used as a test set only once. In the testing procedure, sensitivity was calculated on a per-polyp basis: if there were multiple detections for one polyp, any correctly identified detection of the polyp was considered as correctly classifying the polyp. Based on the three-fold cross-validation results, the bivariate binormal ROC curves were estimated for the two data sets using ROCKIT software available from Kurt Rossmann Laboratories of The University of Chicago.

Example 46

Exemplary Results: Implementation B and Implementation C

Figure 26:
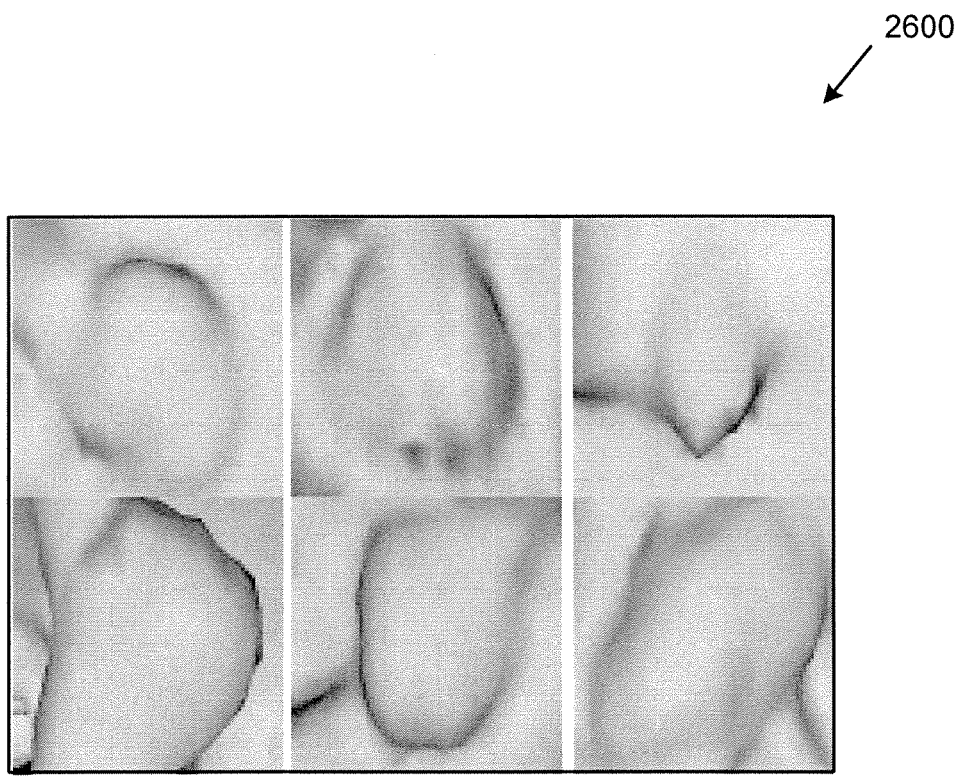
FIG. 26 includes a variety of two-dimensional images of true polyps generated via the technologies described herein.
Figure 27:
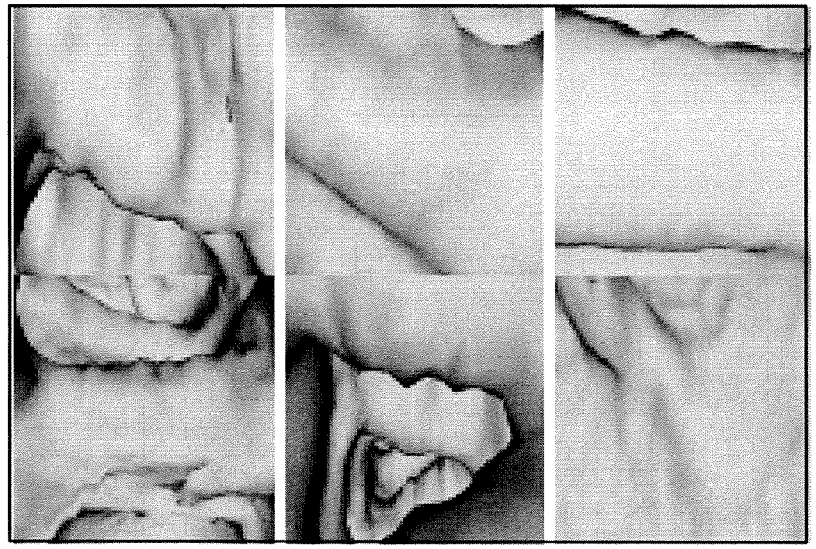
FIG. 27 includes a variety of two-dimensional images of false positive polyp candidates generated via the technologies described herein.

FIGS. 26 and 27 show two-dimensional images generated by the CTC CAD program for true polyps 2600 and false positives 2700, respectively.

Figure 28:
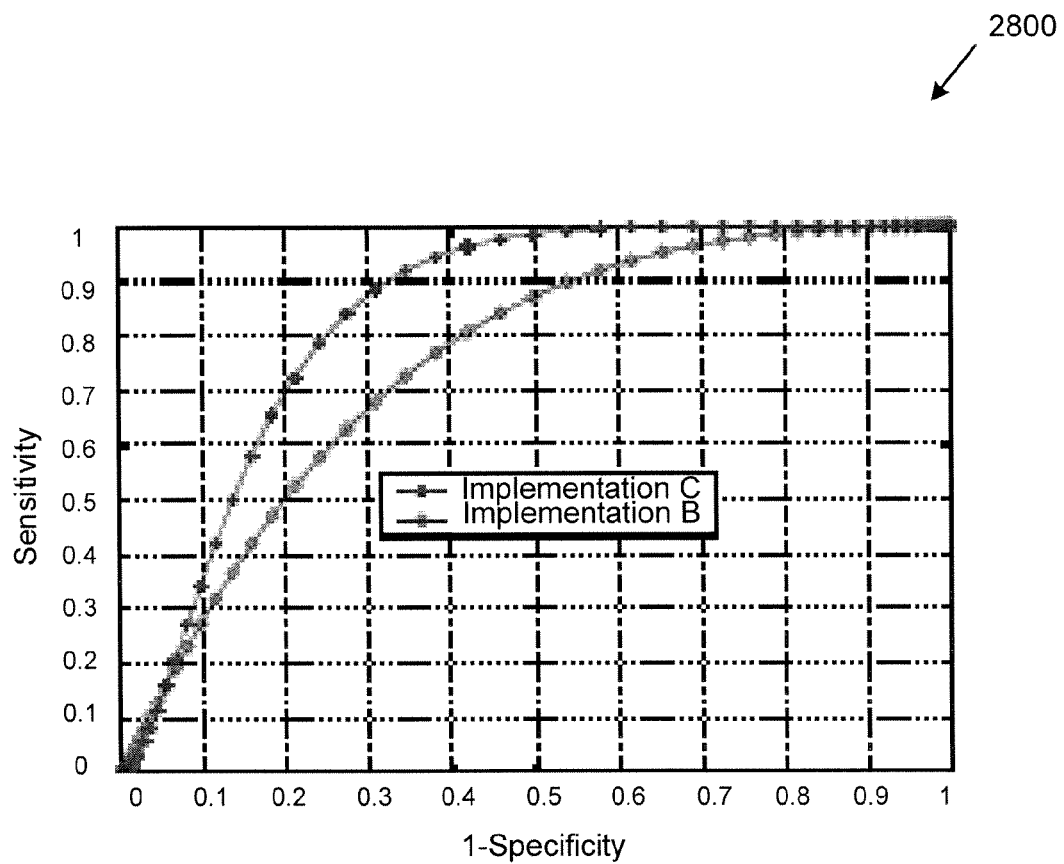
FIG. 28 is a plot of exemplary receiver operating characteristic (ROC) curves of two different technologies for determining whether a polyp candidate is a polyp as described herein.

FIG. 28 shows two ROC curves, where the red (top) curve is for Implementation C and the blue (bottom) curve is for Implementation B. In the plot 2800, the sensitivity scale goes from 0 to 1 (by tenths), and the 1-Specificity scale goes from 0 to 1 (by tenths). The parametric area estimate ($A_z$) for Implementation C is 0.837 with a 95% confidence interval of (0.782,0.883), while the $A_z$ for Implementation B is 0.73 with a 95% confidence interval of (0.666, 0.824). The difference between the two $A_z$'s is 0.086 with a 95% confidence interval of (0.006, 0.165), and a 2-tail p value of 0.034 shows statistically superior performance for Implementation C at a significance level of 0.05.

Figure 29:
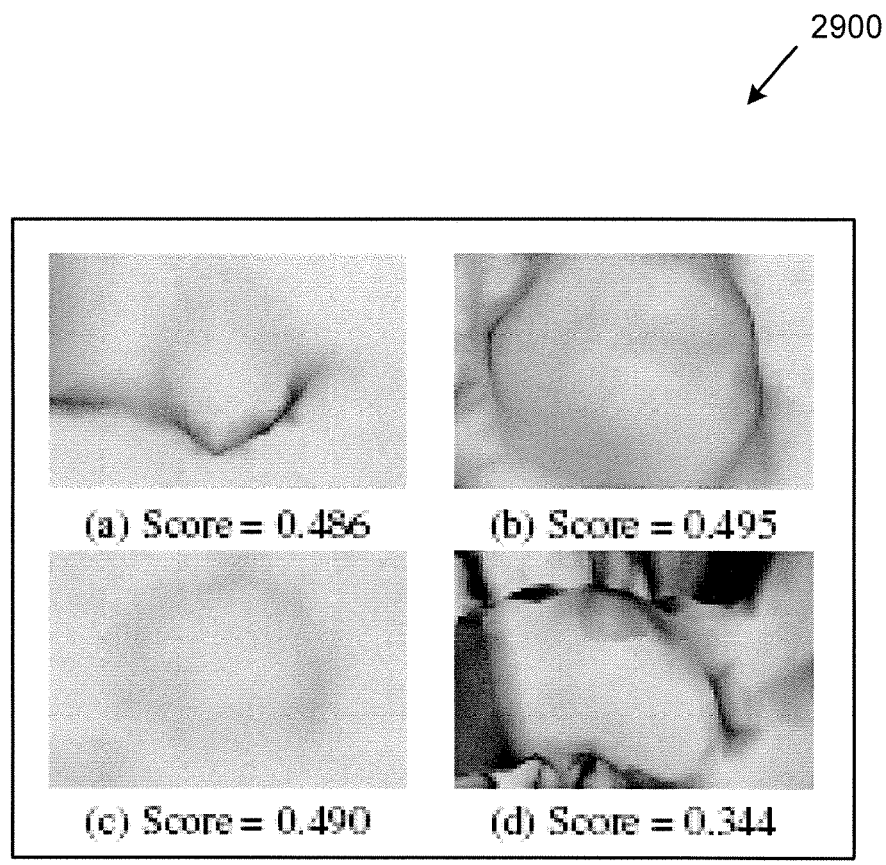
FIG. 29 includes a variety of two-dimensional images of polyps that are challenging to distinguish as polyps.

FIG. 29 shows all four true polyp images 2900 in the data set that had scores lower than 0.5 in the cross-validation for Implementation C. There were nine polyps with scores lower than 0.5 for Implementation B. The result for Implementation C at a classification threshold of 0.5 produced a sensitivity of 95.7% (missing 4 polyps) and a specificity of 70.7%. However, if the threshold were relaxed to 0.485, we obtained a sensitivity of 96.4% (missing 1 polyp) and a specificity of 69.1%. This means that we can reduce false positives by 69.1%, excluding 348 from the 492 false positives, with a cost of 1 missed true polyp.

Example 47

Exemplary Result Discussion Implementation B and Implementation C

The application of a two-dimensional wavelet analysis for the three-dimensional problem is a new idea for polyp detection in virtual colonoscopy. Accurate interpretation of two-dimensional CT scans to identify polyps is a challenging task for a radiologist and requires extensive training. There is evidence that by navigating two-dimensional endoluminal projections of a three-dimensional colon surface constructed from the original two-dimensional CT scans (e.g., a virtual colonoscopy fly-through), radiologists interpret CTC cases more accurately. The technologies described herein can mimic the way radiologists interpret CTC cases and improve upon their interpretation accuracy.

In Implementation C, a floating search method searches the K most predictive neighbors among the 80 available ones for respective wavelet coefficients. In contrast, Implementation B uses a forward method. For prediction, the floating search algorithm was shown to be superior to the forward one, and Implementation C provided better prediction models for the wavelet coefficients.

Ideally, polyp images should score higher than 0.5 while false positives should score lower than 0.5 in the cross-validation. There are some possible explanations for the low scores on four of the polyp images. There is a sharp curve in FIG. 29A due to a tilted camera angle that misleads the classifier. In 29B, the camera was placed too close to the detection so that parts of the polyp were not in the image. In 29C, the polyp was flat and may be difficult for the classifier to identify. Image 29D scored the lowest of the four false negatives; it just does not look like a polyp. This could be caused by a wrong camera position and by holes in the polyp surface due to an unsuccessful colon surface segmentation.

Example 48

Exemplary Conclusion: Implementation B and Implementation C

The wavelet analysis can capture information that is readily apparent to the human eye, such as shape and contour, in a form that can be understood and manipulated by a computer. We showed that feature extraction from wavelet coefficients in Implementation C was able to distinguish real polyps from non-polyp CTC CAD detections, for the more difficult size range of 6-9 mm polyps. Implementation C was able to exclude approximately 69% of the false positives while missing only one true polyp. The technique, if added to the filtering process of a CTC CAD program can improve CAD performance and be incorporated in a tool to aid the radiologist in improving the quality of CTC screening.

Example 49

Exemplary Implementation: Implementation D

An implementation called "Implementation D" comprises four technologies: generating a two-dimensional endoluminal image (e.g., snapshot) for respective polyp detections produced by a CTC CAD system; extracting wavelet texture features for the images; applying a feature selection algorithm to identify a set of useful features; and using the selected features with an SVM committee classifier to classify the CTC CAD detections as polyps or non-polyps. The features from Implementation D can be implemented into any of the other implementations discussed herein.

Example 50

Implementation D: Generating Two-dimensional Images for Polyp Detections

In virtual colonoscopy, a virtual camera can fly through the inside of the colon to examine the inner colon surface while the colonic surface is rendered on a computer screen by endoluminal projection. If a suspicious region is found, radiologists can adjust the camera's view angle and distance to further examine the polyp candidate. In Implementation D, a snapshot of the polyp candidate is taken at an optimized camera position, the snapshot image is analyzed through a wavelet method. The method can mimic the radiologist's reading process.

Example 51

Implementation D: Taking Snapshots of Polyp Candidates

FIG. 11 shows a representation of a colon segment that has a polyp candidate arising from the colon wall. In order to obtain a two-dimensional image that contains as much of the polyp surface information as possible, two parameters can be optimized: position of the camera (e.g., viewpoint) and direction of the lighting. One optimization technique is to use maximized entropy to maximize both viewpoint and lighting direction.

Example 52

Implementation D: Viewpoint Entropy

The quality of a viewpoint can be related to how much object information is contained in the resulting image, as represented by Shannon's entropy. Viewpoint optimality can be evaluated using viewpoint entropy. For example, viewpoint entropy as formulated by Vazquez et al., "Viewpoint Selection using Viewpoint Entropy," in *Proceedings of Vision Modeling and Visualization Conference* (VMV 2001), 2001, pp. 273-280, can be used. The original definition of viewpoint entropy is based on perspective projections. However, the formulation can be extended to also handle orthogonal projections. Thus, orthogonal projection can be used for efficiently calculating viewpoint entropy.

FIG. 13 shows the orthogonal projection of one object represented by a three-dimensional triangular mesh. For a projection direction $\vec{P}_c$, the viewpoint entropy can be defined as $$E(\vec{P}_c) = -\sum_{i=0}^{N_f} \frac{A_i}{S} \log_2 \frac{A_i}{S} \qquad (9)$$

where $N_f$ is the total number of faces in the given 3D mesh, $A_i$ is the visible projection area of the ith face, $A_0$ denotes the background area, and S the sum of the projected area. Note that $E(\vec{P}_c)$ becomes larger when the viewpoint balances face visibility. The task of viewpoint optimization can be to find the viewpoint that achieves the maximum value of viewpoint entropy.

Example 53

Implementation D: Locating a Good Viewpoint

A perspective camera can be used to take a snapshot for each polyp candidate. The camera position can be determined in two steps. The best camera direction is sought first followed by the appropriate camera distance. Virtual lighting direction can also have a big effect on the recognition accuracy for the detections. Lighting direction can be optimized based on the image entropy criterion, which can measure the amount of information contained in the image. Different lighting directions when taking snapshots result in different shadows in the images that have different values of image entropy.

An image having a uniformly distributed intensity histogram has the maximum image entropy. However, experiments showed that the image entropy criterion need not be relevant to recognition accuracy because of the complicated surrounding of the candidate polyp. The background in the two-dimensional snapshot images usually contributed more to the image entropy than that of the polyp area in the images. Thus, the virtual lighting direction can be set as the same as the camera direction to keep a consistent lighting condition for the polyp candidates.

In finding the optimal viewpoint, the view sphere surrounding the object can be usually uniformly sampled, and the viewpoint entropy for viewpoints on the sphere can be calculated to identify the optimal viewpoint (e.g., out of those considered) that maximized entropy. For a particular viewpoint, the viewpoint entropy can be obtained by utilizing graphics hardware: the projected area of a face can be obtained by counting the number of pixels belonging to that face after the object is drawn into the frame buffer. Different faces can be discriminated by assigning different colors for respective faces to establish a one-to-one correspondence between the faces and the colors.

Viewpoint optimization can be sped up by calculating the viewpoint entropy directly on triangle faces of the polyp candidate mesh. The polyp candidate usually includes a few number of vertices (e.g., less than 100) so that traveling the face in the mesh is very efficient.

The camera position can also be limited to be either along the colon centerline or along the average normal to the polyp candidate surface. Such an approach can further reduce the viewpoint search space. Such an approach can also minimize potential blind spots because the polyp candidate can be viewed ahead or behind and substantially reduces search space. Such an approach can be implemented via the arrangements shown in FIG. 15 and FIG. 19.

Additional processing for a method 1900 shown in FIG. 19 can be implemented as follows. At 1920, the polyp centroid C is obtained by averaging the coordinates of the vertices in the surface of the polyp candidate. The nearest point D on the centerline to the point C can be identified by evaluating the Euclidean distance from C to the points on the centerline.

It is possible that the nearest point on the centerline does not see the polyp candidate when the colon makes a sharp bend. In order to avoid such a situation, evaluation of centerline points can be limited to those on the positive side of the polyp candidate. A vector can be formed that points from the candidate's centroid to the centerline point under evaluation. If the angle between the vector and the average normal is less than a threshold (e.g., 90°), the centerline point can be considered to be located in the positive side of the detection and therefore is a valid centerline point. Otherwise, the centerline point can be skipped.

At 1930, to locate a good viewpoint along the centerline, the search space is extended from point D to points B and E which are located approximately ±n cm (e.g., ±5 cm) about D. The line between B and E can be quantized into n (e.g., 100) equally spaced points. Experiments show that 100 centerline points are enough to find a good viewpoint along the centerline.

At 1940 and 1950, to save computation time, two stages are used for searching for the optimal viewpoint. The search is started with course resolution. The viewpoint entropy is calculated for every nth (e.g., fifth) centerline point from B to E and the point with maximal entropy is defined as the coarse optimal viewpoint $P_c$. After $P_c$ is located, it is refined to $P_f$ by evaluating the viewpoint entropy of the n (e.g., four) closest centerline points on either side of $P_c$ and choosing the one with the maximum entropy. FIGS. 17 and 18 show how viewpoint entropy can be calculated, where the three-dimensional triangular mesh represents a candidate polyp surface that has a set of vertices $\{V_j\}_1^{N_v}$ and faces $\{F_1\}_1^{N_f}$. The entropy of one viewpoint, $P_c$, can be calculated using equation (9), where the projected area $A_i$ for the ith face is, $$A_i = A_{oi} \cdot \frac{\overrightarrow{CP_c} \cdot \overrightarrow{N_i}}{|\overrightarrow{CP_c} \cdot \overrightarrow{N_i}|} \qquad (10)$$

where $A_{oi}$, C, and $\overrightarrow{N_i}$ are the area, polyp centroid, and normal of face i, respectively. In the case that the ith face is not visible in the resulting image, we set $A_i=0$. Note that $A_i$ can be the orthogonal projected area of the ith face because the relative location of face i and the centroid C need not be considered.

The following can be defined: $A_0=S_t-S$, where $S_t$ is the total area of the polyp three-dimensional mesh. By such a definition, only the detected three-dimensional mesh of the polyp candidate is involved in the viewpoint entropy calculation. Therefore, background information is eliminated around the polyp candidate during the viewpoint optimization.

At 1960, the viewpoint entropy at the point $P_N$, which is n cm (e.g., 1 cm) along the average normal of the candidate polyp. The final optimal point is identified as either $P_f$ or $P_N$, whichever achieves the maximum viewpoint entropy.

At 1970, the camera distance camDist can be determined by the size of a bounding box calculated for the candidate polyp. A principal component analysis method can be used to calculate three-dimensional bounding boxes for respective polyp candidates, and using the maximum dimensional size $L_{bounding}$ of the box as the initial estimation of the camDist (i.e., camDist=$L_{bounding}$). It is possible that the initial polyp candidate is either bigger or smaller than the true polyp. We then set camDist=0.9 cm if $L_{bounding}$ is less than 0.9 cm, and set camDist=1.1 cm if $L_{bounding}$ is greater than 1.1 cm.

Given the parameter settings of the camera, the resulting snapshot can cover a square area with a length from 7.5 to 9.1 mm for each side such that the viewable area can accommodate polyps in the 6-9 mm size range of interest.

At 1980, a snapshot of the polyp candidate is taken from the optimized camera position. When taking the snapshot, the focal distance of the camera can be set as the camera distance and the height angle as 45°.

Example 54

Exemplary Texture Analysis

An experienced radiologist can fairly easily discriminate false positives from real polyps by examining the projected two-dimensional images of the colon surface, because false positives and true detections contain different shape or texture patterns. One possible texture analysis technique is to apply a wavelet feature extraction method.

Example 55

Exemplary Alternative Feature Extraction for Implementation A

Figure 30:
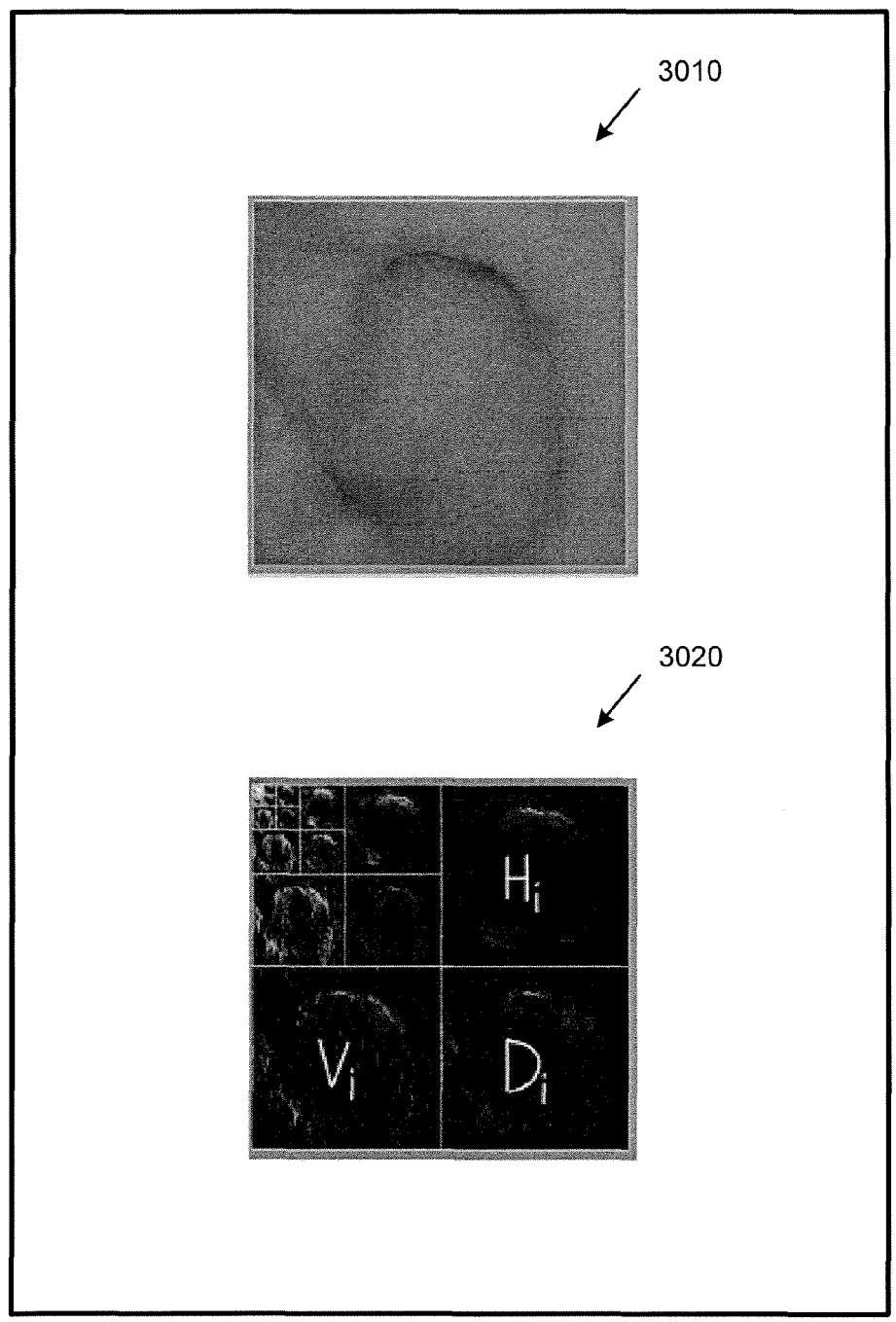
FIG. 30 is a projection image of a polyp candidate and wavelet decomposed images of the projection image.

Wavelet decomposition can split the frequency space into multiple scales and orientations. $V_i(x,y)$, $H_i(x,y)$, and $D_i(x,y)$ can be used to denote the wavelet coefficients in the vertical, horizontal, and diagonal directions at level i. An image can first be decomposed using a five-level wavelet transformation. FIG. 30 includes a projection image 3010 of a polyp candidate (e.g., a true polyp) and wavelet decomposed images 3020 of the projection image and shows one example of five-level wavelet transformations. $V_i(x,y)$, $H_i(x,y)$, and $D_i(x,y)$ denote the wavelet coefficients in the vertical, horizontal, and diagonal directions at level i.

Lyu's feature extraction can be used. Lyu first computed four statistics (mean, variance, skewness, and kurtosis) for each orientation at levels 1-3, yielding 36 features. Lyu then calculated another four similar features for prediction errors of each of those subbands, obtaining a total of 72 features. The prediction errors are based on the concept that the magnitudes of the wavelet coefficients are correlated to their spatial, orientation, and scale neighbors. The magnitude of one coefficient can be predicted by a set of its neighbors. The magnitude of $V_i(x,y)$ may be given by $$|V_i(x, y)| = \sum_{k=1}^{K} w_k |S(k)| \qquad (11)$$

where $w_k$ denotes scalar weights for the neighbor $S(k)$, $S(k)$ represents the kth neighbor of $V_i(x,y)$, and $|\cdot|$ denotes magnitude. A search for the 8 most predictive neighbors by a step-forward method in the following 80 neighbors was done to minimize the prediction error within each subband:

$$V_i(x-c_x, y-c_y), H_i(x-c_x, y-c_y), D_i(x-c_x, y-c_y),$$
$$V_{i+1}\left(\frac{x}{2}-c_x, \frac{y}{2}-c_y\right), H_{i+1}\left(\frac{x}{2}-c_x, \frac{y}{2}-c_y\right), D_{i+1}\left(\frac{x}{2}-c_x, \frac{y}{2}-c_y\right)$$
$$V_{i+2}\left(\frac{x}{4}-c_x, \frac{y}{4}-c_y\right), H_{i+2}\left(\frac{x}{4}-c_x, \frac{y}{4}-c_y\right), D_{i+2}\left(\frac{x}{4}-c_x, \frac{y}{4}-c_y\right),$$

where $c_x=\{-1,0,1\}$ and $c_y=\{-1,0,1\}$. Let the vector $\vec{V}$ contain the coefficient magnitudes of $V_i(x,y)$ strung out into a column vector. After finding the K (e.g., 8) most predictive neighbors, the log predictive error can be calculated as $$\vec{E}(\vec{w}) = \log_2(\vec{v}) - \log_2(|Q\vec{w}|), \quad (12)$$

where matrix Q contains the chosen neighbors, and $\vec{w}$ was determined by a least square algorithm.

Example 56

Exemplary Alternative Feature Extraction for Implementation C

The feature extraction described in Example 42 can be used. The 150 features for the image can include 96 (i.e., 16×6) statistics of the coefficients in respective subbands. In the example, a subband has 6 features, and there are 16 subbands in total. Also included can be 54 (i.e., 9×6) error statistics for the subbands in levels 103. In the example, a subband has 6 features, and there are 9 subbands in levels 1-3.

Example 57

Exemplary Feature Subset and Committee Selection

For the respective polyp candidate images, Implementation B has 72 features, and Implementation C has 150 features. However, some of the features are based on heuristic techniques and were eventually found not to be useful. Irrelevant features can be removed to avoid complexity and overtraining.

A wrapper type feature selection method can be used, where an SVM classifier as described herein can be utilized for fitness evaluation to limit the number of features. The fitness value of a feature can be defined as the average of the sensitivity and specificity of the involved SVM. If it is desired to select m features for an SVM classifier in the committee, a group of vectors with m features can be first randomly selected. During the selection procedure, a feature in the vector can be replaced with a new feature, where the substitution is kept only if it improves the fitness value. The process can be iterated on respective features of the vector (e.g., until no further improvements are found). Such an approach can perform similarly to a genetic algorithm.

The feature selection technique can generate a large number of vectors with m features each. The top $n_f$ (e.g., 1000) feature vectors can be maintained according to their fitness values. In the SVM committee selection procedure, if it is determined that a committee classifier with $n_m$ SVM members is good for the given data, the best committee classifier with $n_m$ SVM members is then found among those $n_f$ combinations.

Example 58

Exemplary Polyp Candidate Classification

An SVM committee classifier can be utilized for polyp candidate classification. A committee classifier can often achieve a better performance than that of its individual committee members. The behavior of outliers can be controlled because committee members with diverse properties are less likely to make the same error in all members.

Exemplary SVM Classifier

Given a set of data pairs $\{x_p, i_p\}_{p=1}^N$, where $x_p \in R^N$ is the feature vector extracted from a polyp candidate image, $i_p\{+1,-1\}$ is a class label (true polyp, true negative) associated with $x_p$. An SVM defines a hyperplane $$f(x) = w^T\phi(x) + b = 0 \quad (13)$$

separating the data points into two classes. In equation (13), w and b are the plane parameters, and $\phi(x)$ is a function mapping the vector x to a higher dimensional space. The hyperplane (13) can be determined using a Structural Risk Minimization technique. For example, the following optimization problem can be solved:

$$\min_{w,\phi,\xi}\left(\frac{1}{2}w^Tw + C\sum_{p=1}^{N_c}\xi_p\right) \quad (14)$$

subject to $$i_p(w^T\phi(x_p)+b) \geq 1-\xi_p, \xi_p \geq 0 \quad (15)$$

here C is a penalty parameter and $\xi_p$ a slack factor. After the hyperplane is determined, a polyp is declared if $f(x_p)>0$, otherwise a non-polyp (e.g., false positive) is declared. In order to combine the outputs from the different committee members, a technique can transfer the SVM output, $f(x_p)$, to a posterior probability by fitting a sigmoid $$p(i_p = 1 \mid f(x_p)) = \frac{1}{1+\exp(Af+B)} \quad (16)$$

The parameters A and B can be fit using a maximum likelihood estimation from a training set $\{f(x_p), i_p\}$ by minimizing a cross-entropy error function.

There exist many ways to combine the outputs of committee members. Theoretic analysis shows that the sum rule (e.g., a simple average) outperforms other combinations schemes in practice (e.g., based on the most restrictive assumptions). The sum rule is superior because it can be most resilient to estimation errors. Therefore, a simple average method can be used to combine the posterior probability of each SVM member to form the final decision (e.g., the decision of the committee members as a whole).

Example 59

Exemplary Experiments

The two wavelet-based texture analysis approaches (Implementation B and Implementation C) were applied and compared as part of a CTC CAD system. The two approaches were compared based on four-fold cross-validation ("CV")

and free-response receiver operating characteristic (FROC) analysis. Statistical analysis was also done on Implementation C using a bootstrap technique, to determine if Implementation C could significantly reduce the false positives produced by the CTC CAD system.

Data Selection

Supine and prone CTC was performed on 44 patients with a high suspicion of colonic polyps or masses. All patients had at least one polyp, and each polyp was verified by follow-up optical colonoscopy. The patients were chosen from a larger cohort who underwent contrast-enhanced CTC. Selection criteria included patients having at least one polyp greater than 5 mm. The majority of the polyps were identified on both the prone and supine views. In this study, only polyps with a size from 6 to 9 mm were of interest. The range is of particular interest because CAD had previously been shown to have a high sensitivity (89.3%) and low false positives (2.1 false positives per patient) for identifying 1 cm or larger polyps.

There were 43 unique 6-9 mm colonoscopy confirmed polyps for the 44 patients, where polyp size came from same day optical colonoscopy measurement. The CTC CAD system detected 32 of these 6-9 mm polyps (74.4% sensitivity). Most of the unidentified polyps were missed in the initial polyp detection stage on the colon surface. Some of the missed polyps were very difficult to identify because of the noise in the CT images. The 32 unique polyps produced 48 detections because some polyps were identified on both the prone and supine views.

Figure 31:
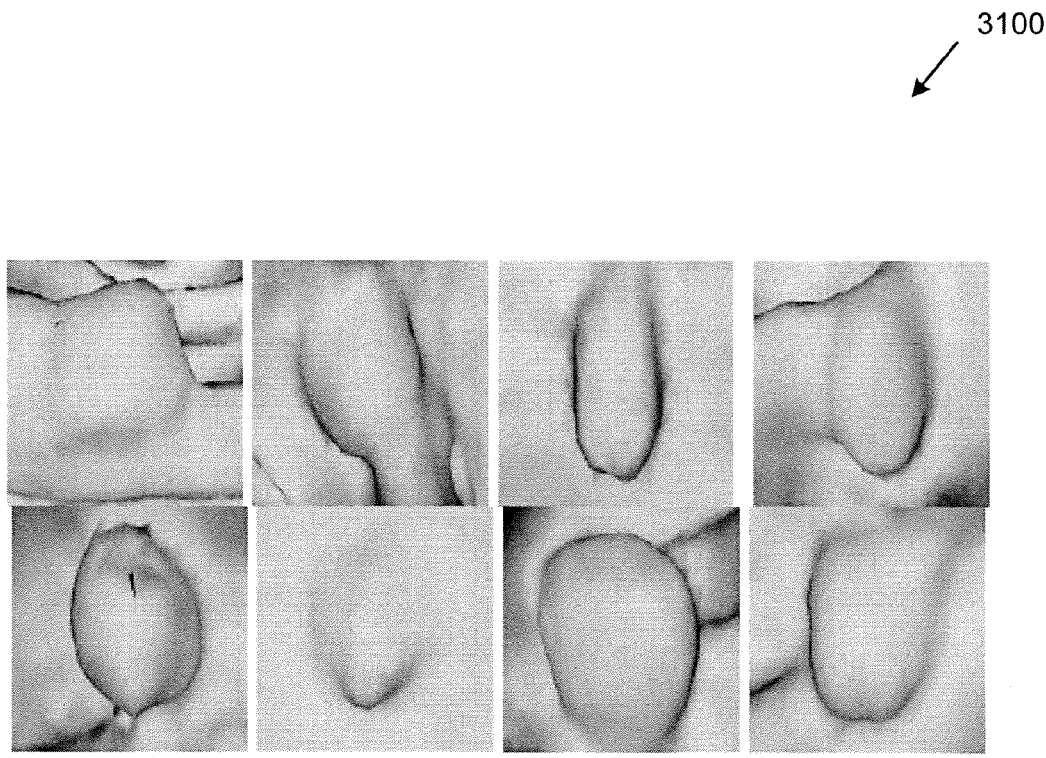
FIG. 31 includes a variety of two-dimensional images of true polyps generated via the technologies described herein.
Figure 32:
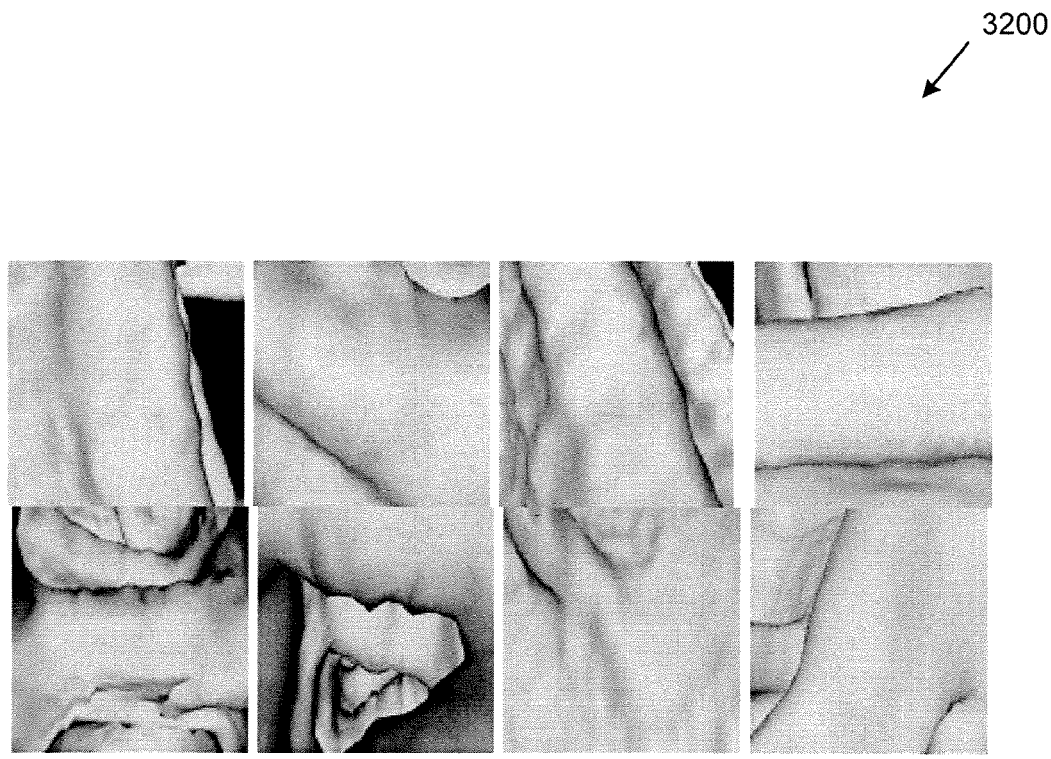
FIG. 32 includes a variety of two-dimensional images of false positive polyp candidates generated via the technologies described herein.

In order to test if the proposed method can effectively reduce false positives produced by the CTC CAD system, we chose one operating point that has a sensitivity of 75% with 11.3 false positives per patient. The selection of operating point was based on an assumption that it would be reasonable that a CTC CAD system should have less than 10 fase positives per patient for detecting 6-9 mm polyps, though an different number could be used. For the chosen operating point, the CTC CAD system produced 35 positive detections for 24 unique polyps and 498 false positives at the chosen operating point. A snapshot of each of the detections (e.g., snapshots 3100 of FIG. 31 show snapshot images taken of true polyps, and snapshots 3200 of FIG. 32 show snapshot images taken of false positives of the CTC CAD system) were evaluated using the techniques described in Examples 50-53. In the following experiments, both Implementation B and Implementation C wavelet analysis techniques were applied to the snapshot images.

Example 60

Exemplary Experiments: Wavelet Analysis and False Positive Reduction (Classifier Configuration)

Implementation B and Implementation C produced 72 and 150 wavelet features, respectively. An SVM committee classifier was used for classification. The number of committee members and number of features used by each member were determined by a brute force search via four-fold CV. The goal was to select a compact model (e.g., committee classifier) that achieved good classification accuracy for the available data set. For reasons of computational efficiency, the search space was restricted to the possible combinations such that each member could use up to seven features, the committee could have up to seven members, and each member used the same number of features. Experiments showed that such a search space covered most of the good combinations.

In four-fold cross-validation, the 44 patients were randomly divided into 4 equal-sized patient cohorts. One of the four cohorts were held out as a test set. The remaining three cohorts were used for the search procedure which led to a trained SVM committee model. The model was then applied to the held-out set to provide test results, and the test results were put into a pool. The training and testing procedures were done four times, using each cohort as a test set (i.e., only once per cohort). At the end, an FROC curve was generated based on the test results pool. Sensitivity was calculated on a per-polyp basis. If there were multiple detections for a polyp, any correctly identified detection of the polyp was considered as correctly classifying the polyp.

The search started by evaluating combinations having from one to seven members per committee, with each member using one feature. The area under the whole FROC curve (AUFC) was then calculated up to 11.3 false positives per patient for each of the configurations and the mean AUFC for all configurations using 1 feature.

The number of features used by the members was then incremented to two. Again, all configurations whose members vary from one to seven and each member using two features were evaluated. The process continued until the mean AUFC began to decrease. The final configuration was selected based on its AUFC. The configuration was selected if it achieved the highest AUFC value.

Example 61

Exemplary Experiments: Statistical Analysis Methods

A test of whether the two wavelet-based feature extraction methods were statistically different and if the proposed strategy could statistically significantly reduce the false positives for detecting 6-9 mm polyps was done. The two wavelet feature methods (e.g., Implementations B and C) were evaluated in terms of their AUFC values by a re-sampling scheme. A bootstrap method was utilized to calculate the 95% confidence interval ("CI") for sensitivity and false positive rate for the chosen operating point on the FROC curve. Features selected for the final SVM committee classifier were examined to better understand which features and which wavelet subbands are particularly important to the analysis.

Example 62

Exemplary Experiments: Results

Two-dimensional Projection Images

FIGS. 31 and 32 show some sample images taken for the true and false positive detections, respectively, using the viewpoint optimization techniques described in Examples 50-53. The images are for the polyp candidates produced by the CTC CAD system that works at the operating point with a sensitivity of 75% and 11.3 false positives per patient. In total, 35 true polyp images were obtained that had 24 unique polyps and 498 false positive images. Color images were produced using the standard lighting and shading method for the polyp detection (e.g., polyp candidate), where each vertex on the colon surface was preset to be a constant color value (e.g., pink). The color images were converted to gray level images as $$I=(11*R+16*G+5*B)/32 \qquad (17)$$

where I is the intensity of the gray image, and R, G, B are intensities of red, blue, and green components in the color image. FIG. 30 shows an exemplary two-dimensional snapshot image (gray image) of a polyp and its 5-level wavelet decomposition.

Two-Dimensional Projection Images

The below table shows the test AUFCs of different committee classifier configurations for data sets extracted by Implementation B.

TABLE

AUFCs for Different Committee Configuration on the Data Extracted by Implementation B (The AUFC is shown in bold for the final selected configuration)

| No. of Features | No. of Members in the Committee Classifier | | | | | | | Mean AUFC |
|---|---|---|---|---|---|---|---|---|
| | 1 | 2 | 3 | 4 | 5 | 6 | 7 | |
| 1 | 8.06 | 8.15 | 7.86 | 8.00 | 8.19 | 8.17 | 7.44 | 7.98 |
| 2 | 8.12 | 8.36 | 8.18 | 8.35 | 8.27 | 8.27 | 8.27 | 8.26 |
| 3 | 8.03 | 8.48 | 8.26 | 8.40 | 8.50 | 8.27 | 8.37 | 8.33 |
| 4 | 8.40 | 8.49 | 8.19 | 8.12 | 8.19 | 8.34 | 8.40 | 8.31 |

The best performing committee classifier for the data was determined as containing five members with each member having three features. The search process stopped when each member in the committee classifier used four features because the mean AUFC started to decrease. Similarly, the following table shows the performances for Implementation C. It was determined that the best performing committee classifier contained five members with each member using four features.

TABLE

AUFCs for Different Committee Configuration on the Data Extracted by Implementation C (The AUFC is shown in bold for the final selected configuration)

| No. of Features | No. of Members in the Committee Classifier | | | | | | | Mean AUFC |
|---|---|---|---|---|---|---|---|---|
| | 1 | 2 | 3 | 4 | 5 | 6 | 7 | |
| 1 | 8.89 | 8.81 | 9.02 | 8.56 | 8.30 | 8.58 | 9.02 | 8.74 |
| 2 | 7.41 | 8.65 | 8.59 | 8.77 | 8.38 | 8.97 | 8.75 | 8.50 |
| 3 | 8.84 | 8.81 | 8.69 | 9.07 | 8.91 | 9.03 | 8.78 | 8.88 |
| 4 | 8.70 | 9.02 | 8.64 | 8.91 | 9.20 | 9.04 | 8.97 | 8.93 |
| 5 | 8.41 | 8.46 | 8.46 | 8.48 | 8.63 | 8.63 | 8.70 | 8.54 |

Cross-Validation Results and Statistical Analysis

Figure 33:
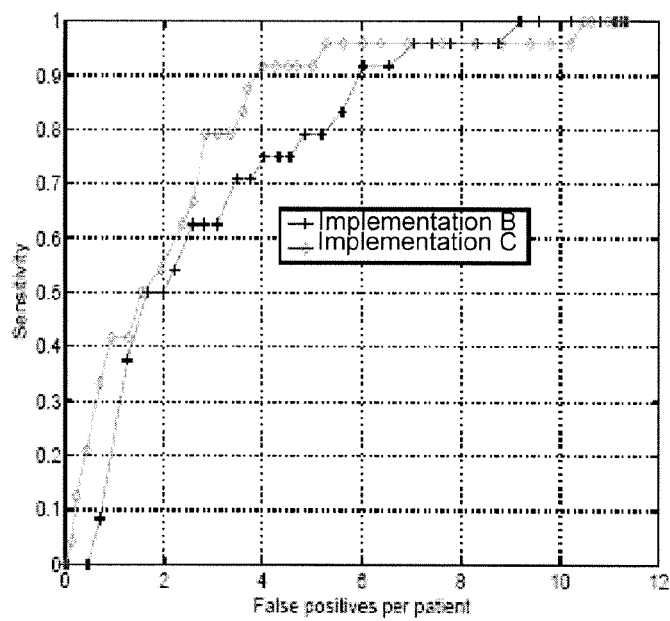
FIG. 33A is a plot of exemplary free-response receiver operating characteristic (FROC) curves of two different technologies for determining whether a polyp candidate is a polyp as described herein.
FIG. 33B is a plot of error bars of a bootstrap result for an enhanced technique involving wavelets.
Figure 33:
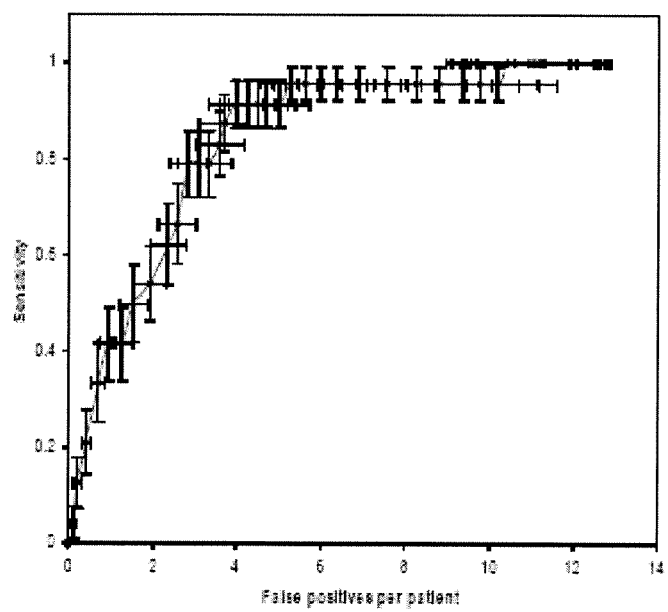

FIG. 33A is a plot of exemplary free-response receiver operating characteristic (FROC) curves for two different feature extraction techniques on polyp candidates produced by a CTC CAD system, where the upper curve is for Implementation C and the lower one is for Implementation B. FIG. 33A shows the two FROC curves for the four-fold cross-validation results on both data sets using the corresponding selected committee classifiers. The AUFC for Implementation B is 8.50, while the AUFC for Implementation C is 9.20. The statistical analysis by re-sampling shows that the difference between the two AUFC (0.7) is statistically significant with a p value of 0.012. From FIG. 33A, it is observed that false positives can be reduced from 11.3 per patient to 5.3 per patient with the cost of one missed true polyp, using Implementation C's wavelet-based feature extraction method. The sensitivity at this operating point is 96% ($23/24$). The false positive rate is 7.1 for Implementation B's technique at a sensitivity of 96%. The false positives are 4.0 and 6.0 for Implementation C and Implementation C's techniques, respectively, if the system works at a sensitivity of 91% ($22/24$).

A bootstrap method was used on the wavelet feature extraction scheme of Implementation C to provide further statistical analysis. The patients were bootstrapped in the test results pool 5,000 times to obtain error bars on the estimates. FIG. 33B shows the error bars on sensitivity and false positive rate for each operating point. The length of error bars are two times the standard deviation associated with the corresponding operating point. One particular point on the FROC was chosen to see if Implementation C can significantly reduce false positives. Using an SVM threshold of 0.44, a mean sensitivity of 91.5% with a 95% confidence interval [83.2%, 99.8%] was produced. The mean false positive rate was 4.69 per patient with 95% confidence interval [3.31, 6.06] for such an SVM threshold; the false positive reduction was significant ($p < 10^{-9}$).

True Polyps with Low Scores

Figure 34:
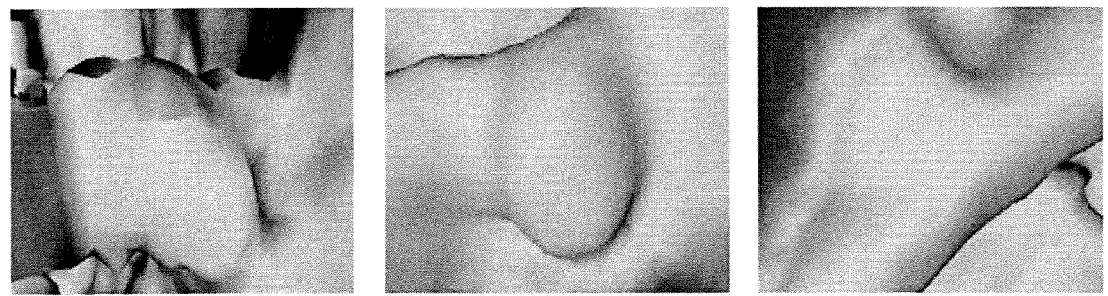
FIG. 34 includes a variety of two-dimensional images of polyps that are challenging to distinguish as polyps.

In the four-fold cross-validation procedure, the trained committee classifier output a probability value (score) of being a true polyp for each candidate. The classifier can assign a value close to "1" for a true polyp detection while a value close to "0" for a false positive. FIG. 34 shows all three true polyp images in the data set which had scores lower than 0.5 in the cross-validation for Implementation C, where (a) had the lowest score (0.18) and (b) and (c) had scores (0.495 and 0.4) close to 0.5. the result for Implementation C at a classification threshold of 0.5 produced a sensitivity of 87.5% ($21/24$) and a false positive rate of 3.7 per patient. However, if the threshold is relaxed to 0.40, there was a sensitivity of 96% ($23/24$) and a false positive rate of 5.3 per patient. In contrast, there were six polyps with scores lower than 0.5 for Implementation B, and a classification threshold of 0.5 produced a sensitivity of 75% ($18/24$) and a false positive rate of 4 per patient.

Selected Features

In the four-fold cross-validation, the feature and committee selection algorithm selected a set of wavelet features from different wavelet subbands. Because different patient cohorts of data were used for the selection in different folds, different sets of features (e.g., they may come from different wavelet subbands) were usually selected in each fold. In the enhanced wavelet feature extraction method of Implementation C, an SVM committee classifier having five members with each member having four features was used. There were 80 feature occurrences in the four-fold cross-validation, with some features reoccurred in multiple committees.

Figure 35:
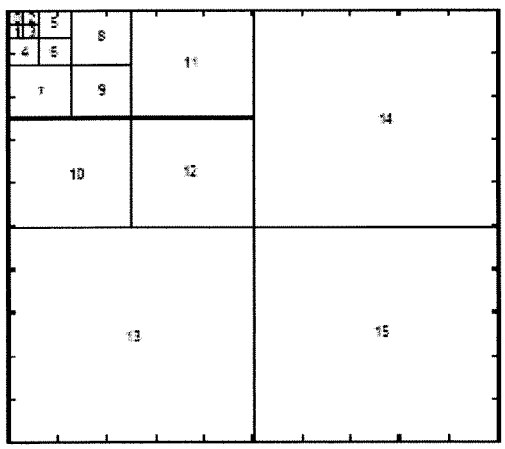
FIGS. 35A-D are plots of indices and features for exemplary wavelet technologies.
Figure 35:
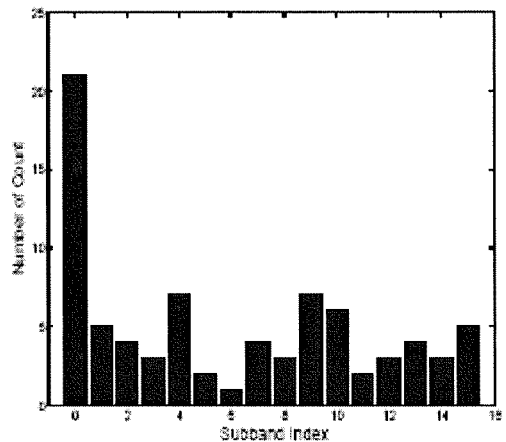
Figure 35:
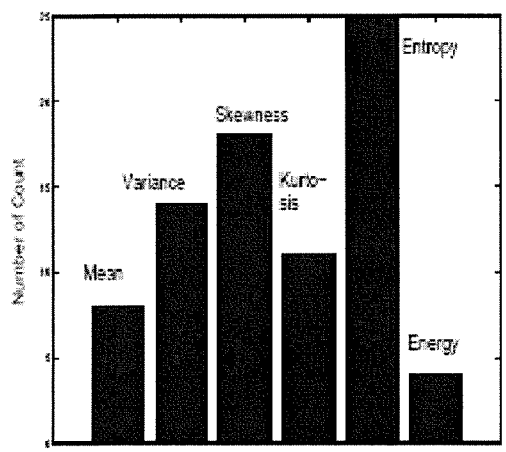
Figure 35:
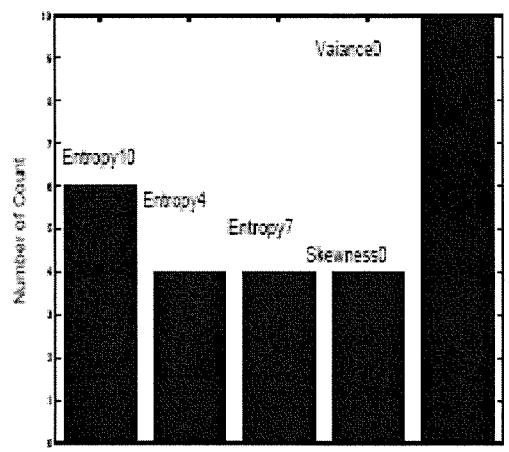

FIG. 35A shows how indices of wavelet subbands for a five-level decomposition are defined. FIG. 35B shows a histogram of occurrence frequencies of the wavelet subbands. The top four most frequently selected subbands were 0, 4, 9, and 10.

The following were calculated: six categories of features for the wavelet coefficients and the prediction errors in each wavelet subband in Implementation C, including mean, variance, skewness, kurtosis, entropy, and energy. FIG. 35C shows a histogram for the six feature categories in the four-fold cross-validation. It is apparent from FIG. 35C that the three most common feature categories in the SVM committee classifier are entropy, skewness, and variance.

FIG. 35D shows the five most frequently appearing individual features in the four-fold cross-validation. The horizontal axis denotes the feature classes, and the vertical axis denotes their frequencies of occurrences in the committee classifier in the four-fold cross-validation. In the figure, "Entropy10" denotes the wavelet coefficient entropy in the $10^{th}$ subband; the same rule applies to the other feature names. In the four-fold cross-validation, the variance of wavelet coefficients in the $0^{th}$ subband appeared ten times. The second most frequently appearing feature was the entropy feature in the $10^{th}$ wavelet subband (6 times), followed by "Entropy4," "Entropy7," and "Skewness0" (4 times each).

Among the eighty feature occurrences in the four-fold cross-validation, fourteen were from the prediction error statistics with the other sixty-six were from the wavelet coefficient statistics.

Computation Time and Entropy Difference

The computation time for a single data case on a PC computer with AMD Athlon MP 2800+(2.13-GHz clock rate), 2 GB RAM, using Microsoft VC++6.0, was less than one minute on average for the chosen operating point. There are about six polyp detections per data case, where the computation time for locating the viewpoint for each detection is 0.1 seconds, and the wavelet analysis for the resulting image of one detection is eight seconds, on average.

It is interesting to show in how many polyp candidates the viewpoint given by the optimal viewpoint along the centerline was preferred to the viewpoint along the average normal and the average entropy difference between the two positions. The following table shows that there are 290 polyp candidates having their optimal viewpoints along the centerline. For the remaining 243 detections, the optimal viewpoints were along the average normal of the polyp candidate.

TABLE

Viewpoint Entropy Given by the Optimal Viewpoint along the CenterLine and along the Average Normal for the Polyp Candidate. The preferred times represent the number of polyp candidates that prefer the viewpoint along the centerline or along the average normal.

|  | Along Average Normal | Along CenterLine |
|---|---|---|
| Mean ± STD | 2.55 ± 1.91 | 2.77 ± 1.89 |
| Preferred times (%) | 290 (54.4%) | 243 (45.6%) |

Example 63

Exemplary Discussion

The techniques herein can interpret CTC cases by analyzing the two-dimensional endoluminal projections rather than the two-dimensional CT slices.

For the wavelet features, the most frequently appearing features come from the $0^{th}$, $4^{th}$, $9^{th}$, and $10^{th}$ wavelet subbands (see FIG. 35B). The $0^{th}$ subband contains low frequency components in the image, and the other three subbands contain relatively low or medium frequency components. This may indicate that the useful discriminative information comes more often from the low and medium frequency range for the identification of 6-9 mm polyps. This concurs with observed experiences where high frequency components are usually considered as noise. Note that the most frequently appearing subband is not necessarily the most discriminative subband, because there are interaction among features from different subbands in the SVM committee classifier. However, we may say that more often appearing subbands are more likely to have discriminating power in the committee classifier.

The entropy features are the most frequently appearing features in the committee classifier, while the energy features are the least frequent (FIG. 35C). These two feature categories were not included in Implementation B. The mean, variance, skewness, and kurtosis worked very well for identifying for forgeries in Lyu but were less useful for identifying polyps. The entropy features turned out to be important for polyp identification. This may be one reason that Implementation C was superior to Implementation B.

A feature selection methodology was useful. Feature selection can evaluate heuristically-developed features and select a compact set of features for the task based on some chosen criterion metrics such as classification accuracy. The feature and committee selection algorithm enabled identification of the useful entropy features. It is possible that different features will be selected when the system is trained on different data.

Implementation C worked as a second classifier to further reduce the CTC CAD polyp detections. One possible rule would be that polyp images should score higher or equal to than 0.5, while false positives should score lower than 0.5 in the cross-validation. Some possible explanations for the three low-scoring polyp images in FIG. 34 are as follows: The image in 34A scored the lowest of the three false negatives because it did not look like a polyp. This could be caused by a bad camera position or by holes in the polyp surface due to an unsuccessful colon surface segmentation. In images 34B and 34C, the polyps touch a fold, making it more difficult for the classifier to identify them. It is difficult for the human eye to identify the polyp in 34C. However, both 34B and 34C obtained scores close to 0.5.

Example 64

Exemplary Wavelet Transformations

The Haar wavelet transformation can be used in any of the examples. However, the Haar wavelet transformation is not scale- and rotation-invariant. Different scales and rotations for one image will lead to different wavelet coefficients and thus different wavelet features. Rotation will possibly have a smaller effect on true polyps than false positives because most of the polyps have a round appearance. There are some techniques for rotation-invariant wavelet transformation. Scale- and rotation-invariant wavelet transformation can be used to implement the techniques described herein.

Example 65

Exemplary Advantages

Implementation C has a potential advantage in that it is relatively insensitive to whether a polyp is or is not on a fold. The camera viewed polyp candidates either from centerline or from the candidate's normal direction, and the camera distance was adjusted to view a 7.5 to 9.1 mm square area on the colon surface. This left only a small area in the resulting image for the background if the candidate was a true polyp. For example, the first and fourth images in the first row of FIG. 31 are true polyps on folds, but the percentage of fold in the image is small.

Bootstrap of the Implementation C technique showed that the technique can significantly reduce false positives by 41.5% in a CTC CAD system for detecting 6-9 mm polyps.

Such so-called "medium-sized" polyps are of particular importance in clinical practice because they are easily missed by radiologists and are difficult for CTC CAD systems to properly detect and classify. Detecting such medium-sized polyps at a low false positive rate can substantially enhance the utility of CTC.

Example 66

Exemplary Description

A post-processing method can reduce false positives for a CTC CAD system. First, a snapshot of each CTC CAD polyp candidate was taken by rendering the colon surface using a set of optimized parameters. An enhanced wavelet analysis technique was then used to extract a set of features for respective snapshots. Finally, a feature and committee classifier selection technique was used to identify a set of good features, and use them in a trained committee SVM classifier to discriminate false positives from true polyps.

Implementation C reduced false positives produced by a CTC CAD system by 41.5% for detecting "medium-sized" colonic polyps. Experiments showed that Implementation C was superior to Implementation B, with the main advantages including the inclusion of entropy features and an efficient floating search algorithm. The technologies described herein can improve CAD performance and the ability of CAD to assist radiologists reading CTC.

Example 67

Exemplary User Interfaces

In any of the examples herein, graphical depiction of a polyp candidate can be displayed to a human classifier (e.g., radiologist), who decides what action, if any, to take. Such interfaces can allow manipulation of the graphical depiction, such as rotation, zooming, and the like.

The interface can highlight (e.g., zoom in on or depict in a special color) areas detected as an anomaly of interest.

Example 68

Exemplary Advantages

As described herein, the technologies can be applied with advantage to process polyp candidates for so-called "medium"-sized polyps, 6-9 mm in diameter.

Example 69

Exemplary Improvements Gained by using Exemplary Embodiments Herein

The embodiments disclosed herein present a filtering technique that can be implemented fully-automatically, and which does not require user interaction.

Example 70

Exemplary Acquisition of Digital Representations

A variety of technologies can be used to acquire three-dimensional digital representations for use with the technologies described herein. In practice, a digital representation of an anatomical structure can be acquired; one or more digital representations of portions of the anatomical structure can then be extracted from the digital representation of the anatomical structure as polyp candidates.

Acquisition of a representation of an anatomical structure is typically done by performing a scan of the soft tissues of the patient. For example, a CT scan can be performed according to any number of standard protocols. CT scans can be used to generate thin-section CT data (for example, helical scan CT data). The representation can be analyzed immediately after the scan, or the representation can be stored for later retrieval and analysis. Exemplary technologies for acquiring scans are described in Pickhardt et al., "Computed Tomographic Virtual Colonoscopy to Screen for Colorectal Neoplasia in Asymptomatic Adults," *New Engl. J. Med.,* 349:2191 (2003), Vining et al., "Virtual Colonoscopy," *Radiology* 193 (P):446 (1994), Vining et al., "Virtual Bronchoscopy," *Radiology* 193 (P):261 (1994), and Vining et al., "Virtual bronchoscopy. Relationships of virtual reality endobronchial simulations to actual bronchoscopic findings" *Chest* 109(2): 549-553 (February 1996).

Any number of hardware implementations can be used to acquire a representation of an anatomical structure. For example, the GE HiSpeed Advantage scanner of GE Medical Systems, Milwaukee, Wis. can be used.

Technologies for classifying a portion as an anomaly of interest (e.g., polyp candidate, polyp, or the like) include analyzing neck characteristics, wall thickness, template matching, and the like. Any other approach capable of detecting anomalies in a representation of an anatomical structure can be used as an alternative.

Additional exemplary segmentation technologies are described in U.S. Pat. No. 6,556,696 to Summers et al., filed Feb. 5, 2002, entitled, "METHOD FOR SEGMENTING MEDICAL IMAGES AND DETECTING SURFACE ANOMALIES IN ANATOMICAL STRUCTURES."

Example 71

Exemplary Computer System for Conducting Analysis

Figure 36:
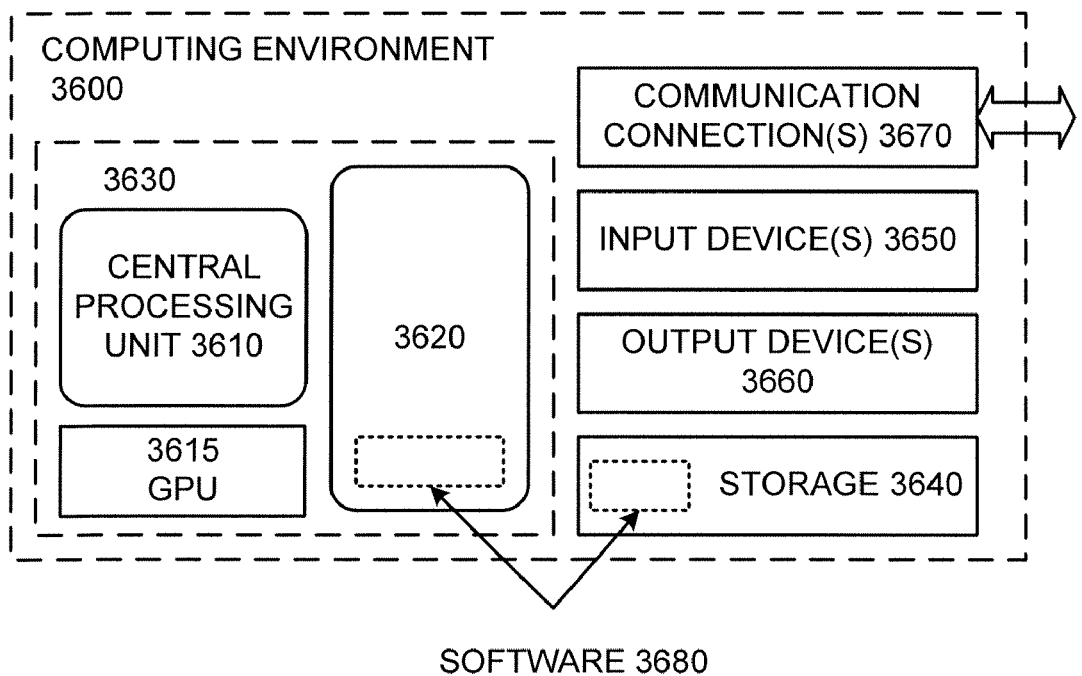
FIG. 36 is a block diagram of an exemplary computer system for implementing the described technologies.

FIG. 36 and the following discussion provide a brief, general description of a suitable computing environment for the software (for example, computer programs) described above. The methods described above can be implemented in computer-executable instructions (for example, organized in program modules). The program modules can include the routines, programs, objects, components, and data structures that perform the tasks and implement the data types for implementing the technologies described above.

While FIG. 36 shows a typical configuration of a desktop computer, the technologies may be implemented in other computer system configurations, including multiprocessor systems, microprocessor-based or programmable consumer electronics, minicomputers, mainframe computers, and the like. The technologies may also be used in distributed computing environments where tasks are performed in parallel by processing devices to enhance performance. For example, tasks related to measuring characteristics of anomalies of interest can be performed simultaneously on multiple computers, multiple processors in a single computer, or both. In a distributed computing environment, program modules may be located in both local and remote memory storage devices.

The computer system shown in FIG. 36 is suitable for implementing the technologies described herein and includes a computer 3620, with a processing unit 3621, a system memory 3622, and a system bus 3623 that interconnects various system components, including the system memory to the processing unit 3621. The system bus may comprise any of several types of bus structures including a memory bus or memory controller, a peripheral bus, and a local bus using a bus architecture. The system memory includes read only memory (ROM) 3624 and random access memory (RAM) 3625. A nonvolatile system (for example, BIOS) can be stored in ROM 3624 and contains the basic routines for transferring information between elements within the personal computer 3620, such as during start-up. The personal computer 3620 can further include a hard disk drive 3627, a magnetic disk drive 3628, for example, to read from or write to a removable disk 3629, and an optical disk drive 3630, for example, for reading a CD-ROM disk 3631 or to read from or write to other optical media. The hard disk drive 3627, magnetic disk drive 3628, and optical disk 3630 are connected to the system bus 3623 by a hard disk drive interface 3632, a magnetic disk drive interface 3633, and an optical drive interface 3634, respectively. The drives and their associated computer-readable media provide nonvolatile storage of data, data structures, computer-executable instructions (including program code such as dynamic link libraries and executable files), and the like for the personal computer 3620. Although the description of computer-readable media above refers to a hard disk, a removable magnetic disk, and a CD, it can also include other types of media that are readable by a computer, such as magnetic cassettes, flash memory cards, DVDs, and the like.

A number of program modules may be stored in the drives and RAM 3625, including an operating system 3635, one or more application programs 3636, other program modules 3637, and program data 3638. A user may enter commands and information into the personal computer 3620 through a keyboard 3640 and pointing device, such as a mouse 3642. Other input devices (not shown) may include a microphone, joystick, game pad, satellite dish, scanner, or the like. These and other input devices are often connected to the processing unit 3621 through a serial port interface 3646 that is coupled to the system bus, but may be connected by other interfaces, such as a parallel port, game port, or a universal serial bus (USB). A monitor 3647 or other type of display device is also connected to the system bus 3623 via an interface, such as a display controller or video adapter 3648. In addition to the monitor, personal computers typically include other peripheral output devices (not shown), such as speakers and printers.

The above computer system is provided merely as an example. The technologies can be implemented in a wide variety of other configurations. Further, a wide variety of approaches for collecting and analyzing data related to processing anomalies of interest is possible. For example, the data can be collected, characteristics determined and measured, anomalies classified and reclassified, and the results presented on different computer systems as appropriate. In addition, various software aspects can be implemented in hardware, and vice versa.

Example 72

Exemplary Methods

Any of the methods described herein can be performed by software executed by software in an automated system (for example, a computer system). Fully-automatic (for example, without human intervention) or semi-automatic operation (for example, computer processing assisted by human intervention) can be supported. User intervention may be desired in some cases, such as to adjust parameters or consider results.

Such software can be stored on one or more computer-readable media (e.g., storage media or other tangible media) comprising computer-executable instructions for performing the described actions (e.g., causing a computer to perform actions of the methods shown).

Alternatives

Having illustrated and described the principles of the invention in exemplary embodiments, it is noted that the described examples are illustrative embodiments and can be modified in arrangement and detail without departing from such principles. Technologies from any of the examples can be incorporated into one or more of any of the other examples.

In view of the many possible embodiments to which the principles of the invention may be applied, it should be understood that the illustrative embodiments are intended to teach these principles and are not intended to be a limitation on the scope of the invention. We therefore claim as our invention all that comes within the scope and spirit of the following claims and their equivalents.

We claim:

1. One or more non-transitory computer-readable media comprising computer-executable instructions for performing a method comprising:
    receiving a three-dimensional digital representation for a polyp candidate;
    choosing a virtual camera viewpoint for the polyp candidate as a point along a centerline in a virtual colon in which the polyp candidate lies, wherein the viewpoint is chosen using a maximum viewpoint entropy technique;
    applying virtual light from a lighting direction to the polyp candidate;
    generating a two-dimensional projection image of the polyp candidate from the virtual camera viewpoint from the three-dimensional digital representation of the polyp candidate;
    determining whether the polyp candidate is a polyp via processing the two-dimensional projection image, wherein determining whether the polyp candidate is a polyp comprises:
    extracting wavelet features from the image; and
    determining whether the polyp candidate is a false positive via application of the wavelet features to a committee classifier; and
    responsive to determining whether the polyp candidate is a false positive, providing an indication of whether the polyp candidate is a polyp.

2. The one or more computer-readable media of claim 1 wherein:
    determining whether the polyp candidate is a false positive comprises evaluating the wavelet features.

3. The one or more computer-readable media of claim 2 wherein the wavelet features comprise:
    wavelet coefficients in the vertical, horizontal, and diagonal directions.

4. The one or more computer-readable media of claim 2 wherein the wavelet features comprise:
    energy and entropy.

5. The one or more computer-readable media of claim 2 wherein the wavelet features comprise:
    predictive error based on most predictive neighbor wavelet coefficients.

6. One or more non-transitory computer-readable media comprising computer-executable instructions for performing a method comprising:
- receiving a three-dimensional digital representation for a polyp candidate;
- generating a two-dimensional projection image of the polyp candidate from the three-dimensional digital representation of the polyp candidate;
- determining whether the polyp candidate is a polyp via processing the two-dimensional projection image, wherein determining whether the polyp candidate is a polyp comprises processing, via wavelet processing, the two-dimensional projection image generated from the three-dimensional digital representation; and
- providing an indication of whether the polyp candidate is a polyp;
- wherein the wavelet processing comprises extracting a plurality of wavelet-based features from the two-dimensional projection image;
- wherein determining whether the polyp candidate is a polyp comprises evaluating the wavelet-based features;
- wherein the wavelet-based features comprise predictive error based on most predictive neighbor wavelet coefficients; and
- the method further comprises:
- finding most predictive neighbor wavelet coefficients via a piecewise linear orthonormal floating search technique.

7. The one or more computer-readable media of claim 1 wherein choosing a virtual camera viewpoint comprises:
- choosing a point a unit distance away from the polyp candidate along an average normal of the polyp candidate as the virtual camera viewpoint for the projection image.

8. The one or more computer-readable media of claim 1 wherein the maximum viewpoint entropy technique comprises:
- computing viewpoint entropy for the polyp candidate directly from faces of a mesh representing the polyp candidate.

9. The one or more computer-readable media of claim 1 wherein the maximum viewpoint entropy maximization technique comprises:
- eliminating background information around the polyp candidate for the maximum viewpoint entropy technique.

10. The one or more computer-readable media of claim 8 wherein the mesh representing the polyp candidate comprises fewer than 100 faces.

11. The one or more computer-readable media of claim 1 wherein the method further comprises:
- before receiving the three-dimensional digital representation for the polyp candidate, identifying the polyp candidate via a computer-aided detection technique.

12. A method of filtering out a polyp candidate as a false positive, the method comprising:
- receiving a digital representation for the polyp candidate;
- choosing a virtual camera viewpoint for the polyp candidate as a point along a centerline in a virtual colon in which the polyp candidate lies, wherein the viewpoint is chosen using a maximum viewpoint entropy technique;
- applying virtual light from a lighting dire'ction to the polyp candidate;
- taking a two-dimensional virtual projection image of the polyp candidate from the virtual camera viewpoint;
- extracting wavelet features from the image;
- determining that the polyp candidate is a false positive via application of the wavelet features to a committee classifier; and
- responsive to determining that the polyp candidate is a false positive, removing the polyp candidate from a list of polyp candidates.

13. An apparatus for detecting polyps in a digital three-dimensional representation of a colon, the apparatus comprising:
- means for identifying at least one polyp candidate in the three-dimensional representation of the colon;
- means for taking a two-dimensional endoluminal projection image from a virtual camera viewpoint for the polyp candidate, wherein the means is configured to choose the viewpoint based on a viewpoint entropy maximization technique as a point alone a centerline in a virtual colon in which the polyp candidate lies;
- means for applying virtual light from a lighting direction to the polyp candidate;
- means for extracting wavelet features from the two-dimensional endoluminal projection image;
- means for evaluating the wavelet features to determine whether the polyp candidate is a false positive or a true positive via application of a committee classifier; and
- means for, responsive to determining that the polyp candidate is a false positive or a true positive, providing an indication of whether the polyp candidate is a polyp.

* * * * *

UNITED STATES PATENT AND TRADEMARK OFFICE
CERTIFICATE OF CORRECTION

PATENT NO.         : 8,023,710 B2
APPLICATION NO.    : 11/685127
DATED              : September 20, 2011
INVENTOR(S)        : Summers et al.

It is certified that error appears in the above-identified patent and that said Letters Patent is hereby corrected as shown below:

In the Specification

Col. 8, line 39, "starting form the" should read --starting from the--;

Col. 9, line 52, "direction PC." should read --direction $P_c$--;

Col. 11, line 21, "Te best" should read --The best--;

Col. 18, line 32, " $\{x_p, i_p\}_{p=1}^{N}$ " should read -- $\{x_p, i_p\}_{p=1}^{N_v}$ --;

Col. 18, line 34, " $i_p \square \{+1,-1\}$ " should read -- $i_p \in \{+1,-1\}$ --;

Col. 26, line 14, " $\{x_p, i_p\}_{p=1}^{N}$ " should read -- $\{x_p, i_p\}_{p=1}^{N_v}$ --;

Col. 26, line 15, " $i_p \{\{+1,-1\}$ " should read -- $i_p \in \{+1,-1\}$ --.

Signed and Sealed this
Twelfth Day of February, 2013

Teresa Stanek Rea
*Acting Director of the United States Patent and Trademark Office*